(12) United States Patent
Fishman

(10) Patent No.: US 7,064,112 B1
(45) Date of Patent: Jun. 20, 2006

(54) PHARMACEUTICAL COMPOSITIONS COMPRISING AN ADENOSINE RECEPTOR AGONIST OR ANTAGONIST

(75) Inventor: Pina Fishman, Herzliya (IL)

(73) Assignee: Can-Fite Biopharma Ltd., Petach Tikva (IL)

( * ) Notice: Subject to any disclaimer, the term of this patent is extended or adjusted under 35 U.S.C. 154(b) by 440 days.

(21) Appl. No.: 09/700,751

(22) PCT Filed: Sep. 8, 2000

(86) PCT No.: PCT/IL00/00550

§ 371 (c)(1),
(2), (4) Date: Jan. 4, 2001

(87) PCT Pub. No.: WO01/19360

PCT Pub. Date: Mar. 22, 2001

(30) Foreign Application Priority Data

| Sep. 10, 1999 | (IL) | ...................................... 131864 |
| Dec. 23, 1999 | (IL) | ...................................... 133680 |

(51) Int. Cl.
*A01N 43/04* (2006.01)
*A61K 31/70* (2006.01)

(52) U.S. Cl. ......................... 514/46; 514/45; 536/26.7; 536/27.14

(58) Field of Classification Search ................ 514/46, 514/45; 536/26.7, 27.14
See application file for complete search history.

(56) References Cited

U.S. PATENT DOCUMENTS

| 5,688,774 A | 11/1997 | Jacobson et al. |
| 5,773,423 A | 6/1998 | Jacobson et al. |
| 6,048,865 A | 4/2000 | Baraldi |

FOREIGN PATENT DOCUMENTS

| GB | 2 289 218 A | 11/1995 |
| RU | 2071770 C1 | 1/1997 |
| RU | 2071771 C1 | 1/1997 |
| WO | WO 94/21195 | 9/1994 |
| WO | WO 95/02604 | 1/1995 |
| WO | WO 98/50047 | 11/1998 |
| WO | WO99/02143 A2 | 1/1999 |
| WO | WO9902143 | 1/1999 |
| WO | WO 99/06053 | 2/1999 |
| WO | WO99/20284 A1 | 4/1999 |
| WO | WO99/63938 A2 | 12/1999 |
| WO | WO00/15231 A1 | 3/2000 |
| WO | WO00/40251 A1 | 7/2000 |
| WO | WO00/44763 A2 | 8/2000 |
| WO | WO0107060 | 2/2001 |

OTHER PUBLICATIONS

Enrique Rozengurt., Experimental Cell Research, vol. 139, (1982), pp. 71-78.
G. Sandberg et al., Thymus, vol. 3, (1981), pp. 63-75.
Michael G. Collis; Pharmac. Ther., vol. 41, (1989), pp. 143-162.
Luiz Belardinelli et al., Progress in Cardiovascular Diseases, vol. XXXII, No. 1 (Jul./Aug.), 1989, pp. 73-97.
R.B. Gilbertsen; Agents and Actions, vol. 22, 1/2 (1987), pp. 91-99.
Pnina Fishman et al.; Cancer Research, vol. 58, pp. 3181-3187, Jul. 15, 1998, pp. 3181-3187.
Raghvendra Dubey et al.; Circulation, 1997, 96:2656-2666.
U. Soderback et al.; Clinical Science; (1991), vol. 81, pp. 691-694.
Bernard Clarke et al.; International Journal of Cardiology, vol. 23, (1989), pp. 1-10.
Meir Djaldetti et al.; Clin. Exp. Metastasis, 1996, vol. 14, pp. 189-196.
Robert L. Stolfi et al.; Cancer Research, Feb. 1983, pp. 561-566.
Fernando A. Gonzalez; Proc. Natl. Acad. Sci. USA; vol. 87, pp. 9717-9721; Dec. 1990.
Maarteen G. Bouma et al.; Journal of Immunology, 1994, 153: 4159-4167.
Joel Linden; FASEB J. 5: 2668-2676; 1991.
Raghvendra K. Dubey et al.; Hypertension, 1998; 31 [part 2]: 516-521.
Sullivan et al.; Drug Development Research, vol. 45, No. 3-4, pp. 103-113, 1998.
Mittelman et al.; Annals New York Academy of Sciences, vol. 255, pp. 225-234, 1975.
Jacobson et al.; Apoptosis, vol., 4, No. 3, pp. 197-211, 1999.
Ramkumar et al., J. Biol. Chem., vol. 268, No. 23, pp. 16887-16890, 1993 (Abstract).
Sajjadi et al.; J. Immunology, vol. 156, No. 9, pp. 3455-3442, May 1, 1996 (Abstract).
Bouma et al.; J. Immunology, vol. 158, No. 11, pp. 5400-5408, Jun. 1, 1997 (Abstract).
Fishman et al., Drug Dev. Res., vol. 50, No. 1, May 2000, p. 101 (Abstract).
Journal of Cellular Physiology, vol. 183, No. 3, Jun. 2000, pp. 393-398.
Kohno et al.; Biochemical and Biophysical Research Communications, vol. 219, pp. 904-910, 1996.
M.E. Lesch et al., Agents and Actions, vol. 34, No. 1/2, (1991), pp. 25-27, XP-001028566.

(Continued)

Primary Examiner—Patrick Lewis
(74) Attorney, Agent, or Firm—Browdy and Neimark, PLLC

(57) ABSTRACT

Adenosine receptor agonists, particularly an agonist which binds to the A3 adenosine receptor, are used for induction of production or secretion of G-CSF within the body, prevention or treatment of toxic side effects of a drug or prevention or treatment of leukopenia, particularly drug-induced leukopenias; and inhibition of abnormal cell growth and proliferation.

38 Claims, 15 Drawing Sheets

OTHER PUBLICATIONS

Shib P. Dutta et al., Journal of Medicinal Chemistry, vol. 18, No. 8, (1975), pp. 780-783, XP-000653225.
Denis J. Schrier et al., The Journal of Immunology, vol. 145, No. 6, (Sep. 15, 1990), pp. 1874-1879, XP-001024527.
Gary W. Bong et al., J. Clin. Invest., vol. 98, No. 12, (Dec. 1996), pp. 2779-2785, XP-001035234.
Willena M. MacKenzie et al., Cancer research, vol. 54, (Jul. 1, 1994), pp. 3521-3526, XP-000601409.
George L. Tritsch et al., Cancer Biochem. Biophys., vol. 2, (1977), pp. 87-90, XP-001002040.
Richard J. Gualtieri et al., Exp. Hematol., vol. 14, (1986), pp. 689-695, XP-001035203.
Woo-Jung Kim et al., Korean J. of Pharmacology, vol. 31, No. 3, (1995), pp. 333-344, XP-001028606.
Vladimir Shneyvays et al., Drug Development Research, vol. 50, (2000), pp. 324-337, XP-000994767.
P. Fishman et al., European Journal of Cancer, vol. 36, (2000), pp. 1452-1458, XP-001035229.
Silvia D'Ancona et al., Anticancer Research, vol. 14, (1994), pp. 93-97, XP-000994765.
Vickram Ramkumar et al., The Journal of Biological Chemistry, vol. 268, No. 23, (Aug. 15, 1993), pp. 16887-16890, XP-001026481.
Fereydoun G. Sajjadi et al., The Journal of Immunology, vol. 156, (1996), pp. 3435-3442, XP-002916157.
P. Fishman et al., The American Association For Cancer Research, vol. 40, (Mar. 1999), pp. 677, XP-001030826.
Yutaka Kohno et al., Biochemical and Biophysical Research Communications, vol. 219, (1996), pp. 904-910, XP-001028266.
Yao Yao et al., Biochemical and Biophysical research Communications, vol. 232, No. 2, (1997), pp. 317-322, XP-001035137.
Kenneth A. Jacobson et al., Drug Development Research, vol. 45, (1998), pp. 113-124, XP-001035206.
Kenneth A. Jacobson et al., TiPS, vol. 19, (May 1998), pp. 184-191.
P. Fishman et al., Clinical Cancer Research, vol. 5, (Nov. 1999), XP-000993539.
N.I. Perevodchikova (Ed.) Handbook: Antitumor Therapy, Moscow, 1993, pp. 192 and 202.
"Meditsina" Handbook of Oncology, Moscow, 1964, p. 63.

US 7,064,112 B1

PHARMACEUTICAL COMPOSITIONS COMPRISING AN ADENOSINE RECEPTOR AGONIST OR ANTAGONIST

This application is the national phase under 35 U.S.C. § 371 of PCT International Application No. PCT/IL00/00550 which has an International filing date of Sep. 8, 2000, which designated the United States of America.

FIELD OF THE INVENTION

The present invention is generally in the field of cancer and concerns a cancer therapy or a therapy intended to counter the side effect of cancer treatment.

PRIOR ART

The following is a list of prior art which is considered to be pertinent for describing the state of the art in the field of the invention. Acknowledgement of these references herein will be made by indicating the number from their list below within brackets.

1. Linden J. The FASEB J. 5:2668–2676 (1991);
2. Stiles G. L. Clin. Res. 38:10–18 (1990);
3. Stolfi R. L., et al. Cancer Res. 43:561–566 (1983);
4. Belardinelli L. et al. Prog. Cardiovasc. Dis. 32:73–97 (1989);
5. Collis M. G., Pharmacol. Ther. 41:143–162 (1989);
6. Clark B. and Coupe M. Int. J. Cardiol. 23:1–10 (1989);
7. Dubey R. K. et al. Circulation 96:2656–2666 (1997)
8. Soderback U. et al. Clin. Sci. 81:691–694 (1994);
9. Gilbertsen R. B. Agents actions 22:91–98 (1987);
10. Bouma M. G. et al. J. Immunol. 153: 4159–4168 (1994);
11. Rozengurt E. Exp. Cell Res. 139:71–78 (1982);
12. Gonzales F. A., et al., PNAS USA 87:9717–9721 (1990);
13. Sandberg G. and Fredholm B. B., Thymus 3:63–75 (1981);
14. Pastan I. H. et al. Annu. Rev. Biochem. 44:491–495 (1975);
15. WO 99/02143;
16. Fishman P., et al. Cancer Res. 58:3181–3187 (1998);
17. Djaldetti M. et al. Clin. Exp. Metastasis 14:189–196 (1996);
18. Fishman P. et al. Cancer Research 58:3181–3187 (1998).

BACKGROUND OF THE INVENTION

Myelotoxicity is a prevailing, severe, complication of chemotherapy and is one of the factors that limit the administrable dose of the chemotherapeutic drug. It causes more life threatening patient morbidity and actual mortality than any other chemotherapeutic side effect and may result in an increased number of hospital stay days. In addition, drug induced myelosuppression limits the administration of larger, potentially more effective doses of chemotherapy to patients with malignancies. Several approaches to resolve this adverse event have included the use of lithium, prostaglandin E, interferon, lactoferrin and the growth factors granulocyte-macrophage colony stimulating factor (GM-CSF) and granulocyte-colony stimulating factor (G-CSF). To date, use of growth factors such as G-CSF is a standard therapy for cancer patients with neutropenia. It stimulates the proliferation and differentiation of hematopoietic progenitors and also controls the functional activities of neutrophils and macrophages. However, the G-CSF treatment is costly and as it is a recombinant protein, it has accompanying side effects.

Adenosine, an endogenous purine nucleoside, is ubiquitous in mammalian cell types. Adenosine present in the plasma and other extracellular fluids mediates many of its physiological effects via cell surface receptors and is an important regulatory protein. It is released into the extracellular environment from metabolically active or stressed cells. It is known to act through its binding to specific G-protein associated A1, A2 and A3 membranal receptors[1-2]. The interaction of adenosine with its receptors initiates signal transduction pathways, mainly the adenylate cyclase effector system, which utilizes cAMP as a second messenger. While A1 and A3 receptors, which are coupled with Gi proteins, inhibit adenylate cyclase and lead to a decrease in the level of intracellular cAMP, the A2 receptor, which is coupled to Gs proteins, activates adenylate cyclase, thereby increasing cAMP levels[3].

Since specific surface receptors for adenosine are found in nearly all cells, almost all organ systems of the body are regulated to some extent by its local release. This includes regulation of the electrophysiological properties of the heart, sedation and suppression of neurotransmitter's release and regulation of rennin release and vascular tone in the kidney[4-7]. Adenosine exerts various effects on the immune system including anti-inflammatory activity through the inhibition of cytokine release, inhibition of platelet aggregation, induction of erythropoietin production and modulation of the lymphocyte function[8-10]. Further, adenosine was found to play a role in the modulation of some central nervous system (CNS) functions, in wound healing, in diuresis and in controlling pain. It was also demonstrated that adenosine is capable of inducing proliferation in a wide range of normal cell types[11-14]. This modulation of cell growth is likely mediated through the adenylate cyclase effector system described above.

In a recent study it was found that adenosine acts as a chemoprotective agent, which activity is likely related to its capability to stimulate bone marrow cell proliferation. Further, it was found that adenosine exerted an inhibitory effect on the proliferation of tumor cells, apparently through G0/G1 cell cycle arrest and reduction of the telomeric signal[17-18]. The dual effect has turned adenosine into an attractive concept for cancer treatment.

SUMMARY OF THE INVENTION

In accordance with the present invention it was found that adenosine A3 receptor agonists (A3RAg) have a dual effect in that they inhibit proliferation of malignant cells on the one hand, and counter toxic side effects of chemotherapeutic drugs on the other hand. Specifically, the A3RAg compounds inhibit proliferation and growth of tumor cells, synergize with an anti-tumor cytotoxic drug in reducing the tumor load, induce proliferation and differentiation of bone marrow cells and white blood cells and counter toxic side effects of other drugs, particularly chemotherapeutic drugs. Furthermore, it was discovered in accordance with the invention that the A3RAg exerts these activities by a variety of forms of administration including parenteral administration and particularly oral administration. It was further found in accordance with the invention that some of the A3RAg activity may be mimicked by other agonists and antagonists of the adenosine A1 or A2 receptors: the adenosine A1 receptor agonists (A1RAg) shares with the A3RAg its ability to induce G-CSF secretion; adenosine A2 receptor agonist (A2RAg) shares with the A3RAg its ability to inhibit proliferation of malignant cells; and the adenosine A2 receptor antagonist (A2RAn) shares with the A3RAg its ability to counter toxic side effects of drugs, e.g. treat or prevent leukopenia.

The invention relates in its broadest sense, to the use of an active ingredient to yield one of the following therapeutic/biological effects: inducing production or secretion of G-CSF within the body; prevention or treatment of toxic side effects of a drug or prevention or treatment of leukopenia, particularly drug-induced leukopenia; and inhibition of abnormal cell growth and proliferation. The active ingredient may be an A3RAg or an agonist or antagonist of the adenosine receptor system which can yield one of these therapeutic effects, achieved by the use of the A3RAg.

Several embodiments are provided by the invention. The first embodiment, to be referred to herein as the "G-CSF-inducing embodiment" involves the use of an active ingredient, which may be an A3RAg or an A1RAg to yield secretion of the G-CSF within the body of a treated subject. G-CSF is known to stimulate proliferation and differentiation of hematopoietic progenitors and controls the functional activities of neutrophils and macrophages. Thus, a G-CSF-inducing agent such as those mentioned above, may have a high therapeutic value, for example, in countering (i.e. preventing, reducing, or ameliorating) myelotoxicity.

Provided in accordance with this embodiment is a method for inducing G-CSF secretion within the body of a subject, comprising administering to the subject an effective amount of an active ingredient selected from the group consisting of A3RAg, an A1RAg and a combination of an A3RAg and an A1RAg. In accordance with this embodiment there is further provided a method for the therapeutic treatment, comprising administering to a subject in need an effective amount of said active ingredient for achieving a therapeutic effect, the therapeutic effect comprises induction of G-CSF production or secretion. Still further provided by this embodiment is use of said active ingredient for the manufacture of a pharmaceutical composition for inducing G-CSF secretion. Also provided by this embodiment is a pharmaceutical composition for inducing production or secretion of G-CSF within the body, comprising a pharmaceutically acceptable carried an effective amount of said active ingredient.

In accordance with another embodiment of the invention, to be referred to herein at times as the "Leukopenia-prevention embodiment" or more specifically as the "neutropenia-prevention embodiment", an active ingredient which may be an A3RAg, or an A2RAn, is used for the prevention or treatment of leukopenia, which may result from myelotoxicity.

In accordance with this embodiment there is provided a method for inducing proliferation or differentiation of bone marrow or white blood cells in a subject, comprising administering to the subject an effective amount of an active ingredient selected from the group consisting of an A3RAg, an adenosine A2RAn and a combination of an A3RAg or an A2RAn. Also provided by this embodiment is a method for prevention or treatment of leukopenia, comprising administering to a subject in need an effective amount of said active ingredient. Further provided in accordance with this embodiment is use of said active ingredient for the manufacture of a pharmaceutical composition for inducing proliferation or differentiation of bone marrow or white blood cells. Still further provided in accordance with this embodiment is use of said active ingredient for the manufacture of a pharmaceutical composition for the prevention or treatment of leukopenia. The pharmaceutical composition can particularly be used for prevention or treatment of leukopenia.

In accordance with a related embodiment, to be referred to herein as the "toxicity-preventing embodiment" the abovementioned active ingredient (namely one of the A3RAg, or A2RAn, as well as a combination thereof, is used to counter toxic side effects of drugs, such as chemotherapeutic drugs or nemoleptic drugs.

In accordance with this latter embodiment there is thus provided a method for prevention or treatment of toxic side effects of a drug, comprising administering to a subject in need an effective amount of an active ingredient selected from the group consisting of an A3RAg, an A2RAn and a combination of an A3RAg and an A2RAn. Also provided in accordance with this embodiment is use of said active ingredient for the manufacture of a pharmaceutical composition for the prevention or treatment of drug-induced toxicity. Still further provided by this embodiment is pharmaceutical composition for prevention or treatment of toxic side effects of a drug, comprising an effective amount of said active ingredient and a pharmaceutically acceptable carrier.

For the purpose of countering drug-induced leukopenia or drug-induced toxic side effects in general, it is at times desirable to formulate a drug which has such toxic side effects together with said active ingredient for combined administration of the two. The invention thus also provides a pharmaceutical composition comprising, in combination a drug that can cause toxic side effect in a subject treated thereby and said active ingredient; as well as use of said active ingredient for the manufacture of such a pharmaceutical composition. Said active ingredients included in said composition being an amount effective for prevention or treatment of the toxic side effects.

In accordance with yet another embodiment of the invention, to be referred to herein as the "proliferation-inhibiting embodiment", an active ingredient, which may be an A3RAg, an A2RAg, or a combination of the two, is used for selectively inhibiting abnormal cell growth, e.g. tumor cell growth.

In accordance with this embodiment there is provided a method for inhibiting abnormal cell growth in a subject, comprising administering to the subject a therapeutically effective amount of an active ingredient selected from the group consisting of an A3RAg, an A2RAg and a combination of an A3RAg and an A2RAg. Also provided in accordance with this embodiment is use of said active ingredient for the manufacture of a pharmaceutical composition for inhibiting abnormal cell growth. Still further provided by this embodiment is a pharmaceutical composition for inhibiting abnormal cell growth, comprising said active ingredient, and a pharmaceutically acceptable carrier.

In one embodiment of the invention the administration of the active ingredient is intended to achieve dual therapeutic effect: inhibition of abnormal cell growth and reduction of toxic side effects of a drug causing such effects.

The preferred active ingredient in accordance with the invention is an A3RAg. The preferred route of administration of the active ingredient, in accordance with the invention is the oral administration route. However, this preference does not exclude other active ingredients neither other administration routes of the active ingredients.

The dosage of the active ingredient, particularly where the active ingredient is an A3Rag, is preferably less than 100 μg/kg body weight, typically less than 50 μg and desirably within the range of 1–10 μg/kg body weight.

DETAILED DESCRIPTION OF THE INVENTION

In accordance with the invention novel therapeutic use is provided for certain active agents, particularly adenosine receptor agonists and antagonists. By one embodiment, the G-CSF-inducing embodiment, some such agents are used to mediate the production and secretion of G-CSF from cells. In accordance with another embodiment, the toxicity-preventing embodiment, some such agents are used to counter toxic side effects of drugs, e.g. chemotherapeutic or nemoleptic drugs. In a further embodiment, the leukopenia-prevention embodiment, some such agents are used to counter leukopenia, particularly drug-induced leukopenia. In accordance with yet another embodiment, the proliferation-inhibition embodiment, some such agents are used to selectively inhibit abnormal cell growth.

The term "leukopenia" as used herein refers to the reduction in the circulating white blood cell count. While leukopenia is usually characterized by a reduced number of blood neutrophils (neutropenia), at times, a reduced number of lymphocytes, monocytes, eosinophils or basophils may be detected.

Leukopenia which may arise from the reduced production or excessive splenic sequestration of neutrophils, may result from a hereditary and congenital diseases. However it is mainly observed after treatment with drugs, such as cytoreductive cancer drugs, antithyroid drugs, phenothiazines, anticonvulsants penicillins, sulfonamides, and chloramphenicol. Some antineoplastics cause leukopenia as a predictable side effect.

In the following, a reduction in leukocyte count or neutrophil count by drugs will be referred to herein, as "drug-induced leukopenia" or "drug-induced neutropenia". Furthermore, whenever mention is made to leukopenia, it should be understood as referring particularly to "neutropenia".

Further, the term "prevention or treatment of leukopenia" should be understood as a procedure whereby the reduction in leukocyte cell count which may otherwise occur, is reduced, totally prevented or if such reduction has occurred, a procedure which gives rise to increase in the leukocyte cell count. Leukopenia is manifested by a variety of side effects such as an increased possibility to infection by significant infectious agents and others. The term "prevention or treatment of leukopenia" should also be understood as meaning an improvement in such parameters which may occur as a result of leukopenia.

The pharmaceutically or therapeutically "effective amount" for purposes herein is determined by such considerations as may be known in the art. The amount must be effective to achieve the desired therapeutic effect which depends on the type and mode of treatment. As is clear to the artisan, the amount should be effective to obtain the improvement of survival rate, to obtain a more rapid recovery to obtain the improvement or elimination of symptoms or any other indicators as are selected as appropriate measures by those skilled in the art. When, for example, said active ingredient is administered to induce G-CSF production, an effective amount of the active ingredient may be an amount which leads to production and secretion of G-CSF from peripheral blood mononuclear cells, endothelial cell or fibroblast, in which it was produced, thereby, for example, stimulating the maturation of granulocytes progenitors into mature neutrophils. Where the active ingredient is administered to counter drug-induced leukopenia, an effective amount of the active ingredient may be an amount which protects the individual against the drug-induced reduction in the count of leukocytes, particularly neutrophils; an amount of the active ingredient which can give rise to an increase in an already decreased level of such cells, e.g. restore the level to a normal level or sometimes even above; etc. Where the active ingredient is administered in order to reduce toxic side effect of a drug, the amount of the active ingredient may, for example, be an amount effective in reduction of weight loss resulting from the drug administered. Where the active ingredient is administered in order to inhibit abnormal cell growth, as detailed hereinafter, an effective amount may be an amount which will inhibit the proliferation of such cells in the treated subject and even eliminate the tumor. Where the active ingredient is administered in order to potentiate the effect of an anti-cancer chemotherapeutic drug, an effective amount may be an amount which either increases the cancer specific toxicity of the chemotherapeutic treatment; an amount which is effective in reducing the amount of the chemotherapeutic drug or drug combination required to achieve a desired effect of the chemotherapeutic drug or drug combination, i.e. reduction of the tumor load; etc. An example of an effective amount is a daily administration of A3RAg less than 100 µg/kg body weight, typically less than 50 µg/kg body weight and optionally even less than 10 µg/kg body weight, e.g. about 3–6 µg/kg body weight. Such an amount of A3RAg is typically administered in a single daily dose although at times a daily dose may be divided into several doses administered throughout the day or at times several daily doses may be combined into a single dose to be given to the patient once every several days, particularly if administered in a sustained release formulation.

The active ingredient according to the invention is preferably an A3RAg. The A3RAg is any agonist which binds to A3 receptors and activates them to yield a therapeutic effect of the present invention. It should be noted that at times, an A3RAg may also interact with other receptors, e.g. with the A1 and A2 receptors. However, the A3RAg used in accordance with the invention exerts its prime effect through the A3 receptor (namely there may also be minor effects exerted through interaction with other adenosine receptors).

By one embodiment, the active ingredient according to the invention is a nucleoside derivative. By the term "nucleoside" it is meant any compound comprising a sugar, preferably ribose or deoxyribose, or a purine or pyrimidine base or a combination of a sugar with a purine or pyrimidine base preferably by way of N-glycosyl link. The term "nucleoside-derivative" will be used to denote herein a naturally occurring nucleoside as defined hereinabove, a synthetic nucleoside or a nucleoside which underwent chemical modifications by way of insertion/s, deletion/s or exocyclic and endocyclic substitution/s of group/s therein or conformational modifications which provide a derivative with the desired biological effect.

In accordance with one preferred embodiment of the invention the active ingredient is an A3RAg.

According to one embodiment of the invention, the active ingredient is a nucleoside derivative of the following general formula (I):

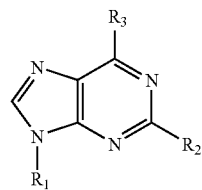

(I)

wherein $R_1$ is $C_1$–$C_{10}$ alkyl, $C_1$–$C_{10}$ hydroxyalkyl, $C_1$–$C_{10}$ carboxyalkyl or $C_1$–$C_{10}$ cyanoalkyl or a group of the following general formula (II):

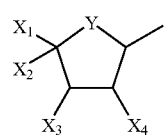

(II)

in which:

Y is an oxygen or sulfur atom or $CH_2$;

$X_1$ is H, $C_1$–$C_{10}$ alky, $R^aR^bNC(=O)$— or $HOR^c$—, wherein $R^a$ and $R^b$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, $C_1$–$C_{10}$ BOC-aminoalkyl, and $C_3$–$C_{10}$ cycloalkyl or are joined together to form a heterocyclic ring containing two to five carbon atoms, and $R^c$ is selected from the group consisting of $C_1$–$C_{10}$ alkyl, amino, $C_1$–$C_{10}$ haloalkyl, $C_1$–$C_{10}$ aminoalkyl, $C_1$–$C_{10}$ BOC-aminoalkyl, and $C_3$–$C_{10}$ cycloalkyl;

$X_2$ is H, hydroxyl, $C_1$–$C_{10}$ alkylamino, $C_1$–$C_{10}$ alkylamido or $C_1$–$C_{10}$ hydroxyalkyl;

$X_3$ and $X_4$ each independently are hydrogen, hydroxyl, amino, amido, azido, halo, alkyl, alkoxy, carboxy, nitrilo, nitro, trifluoro, aryl, alkaryl, thio, thioester, thioether, —OCOPh, —OC(=S)OPh or both $X_3$ and $X_4$ are oxygen connected to >C=S to form a 5-membered ring, or $X_2$ and $X_3$ form the ring of formula (III):

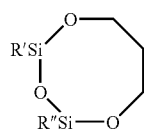

(III)

where R' and R" are independently $C_1$–$C_{10}$ alkyl;

$R_2$ is selected from the group consisting of hydrogen, halo, $C_1$–$C_{10}$ alkylether, amino, hydrazido, $c_1$–$C_{10}$ alkylamino, $C_1$–$C_{10}$ alkoxy, $C_1$–$C_{10}$ thioalkoxy, pyridylthio, $C_2$–$C_{10}$ alkenyl, $C_2$–$C_{10}$ alkynyl, thio, and $C_1$–$C_{10}$ alkylthio; and $R_3$ is an —$NR_4R_5$ group, with $R_4$ being hydrogen, alkyl, substituted alkyl or aryl-NH—C(Z)—, with Z being O, S or $NR^a$ with $R^a$ having the above meanings, and, when $R_4$ is hydrogen, $R_5$ being selected from the group consisting of R- and S-1-phenylethyl, benzyl, phenylethyl or anilide groups, each such group being unsubstituted or substituted in one or more positions with a substituent selected from the group consisting of $C_1$–$C_{10}$ alkyl, amino, halo, $C_1$–$C_{10}$ haloalkyl, nitro, hydroxyl, acetamido, $C_1$–$C_{10}$ alkoxy, and sulfonic acid or a salt thereof; or $R_5$ being benzodioxanemethyl, fururyl, L-propylalanylaminobenzyl, β-alanylaminebenzyl, T-BOC-β-alanylaminobenzyl, phenylamino, carbamoyl, phenoxy or $C_1$–$C_{10}$ cycloalkyl; or $R_5$ being a group of the following formula:

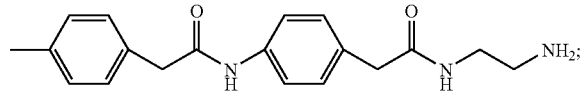

or, when $R_4$ is, alkyl, substituted alkyl, or aryl-NH—C(Z)—, then $R_5$ being selected from the group consisting of substituted or unsubstituted heteroaryl-$NR^a$—C(Z)—, heteroaryl-C(Z)—, alkaryl-$NR^a$—C(Z)—, alkaryl-C(Z)—, aryl-NR-C(Z)— and aryl-C(Z)—, with Z having the above defined meanings;

or a suitable salt of the compound defined above, e.g. a triethylammonium salt thereof.

According to this embodiment of the invention, the active ingredient is preferably a nucleoside derivative of the general formula (IV):

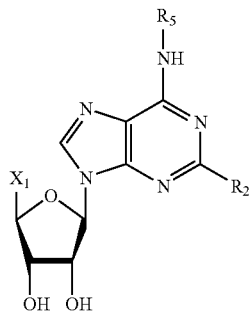

(IV)

wherein $X_1$, $R_2$ and $R_4$ are as defined above.

Preferred active ingredients according to this embodiment of the invention may generally be referred to as $N^6$-benzyladenosine-5'-uronamides and derivatives thereof found to be A3-selective adenosine receptor agonists. Examples for such derivatives are $N^6$-2-(4-aminophenyl)ethyladenosine (APNEA), $N^6$-(4-amino-3-iodobenzyl)adenosine-5'-(N-methyluronamide) (AB-MECA) and 1-deoxy-1-{6-[({3-iodophenyl}methyl)amino]-9H-purine-9-yl)-N-methyl-β-D-ribofuranuronamide, the latter also referred to in the art as $N^6$-3-iodobenzyl-5'-methylcarboxamidoadenosine, $N^6$-(3-iodobenzyl)adenosine-5'-N-methyluronimide and herein above and below by the abbreviation IB-MECA or a chlorinated derivative of IB-MECA ($R_2$=Cl), referred to herein as Cl-IB-MECA, IB-MECA and Cl-IB-MECA being currently particularly preferred.

According to another embodiment of the invention, the active ingredient may be an adenosine derivative generally referred to as $N^6$-benzyladenosine-5'-N-alkyluronamide-$N^1$-oxide or $N^6$-benzyladenosine-5'-N-dialyluronamide-$N^1$-oxide.

Yet further, the active ingredient may be a xanthine-7-riboside derivative of the following general formula (V):

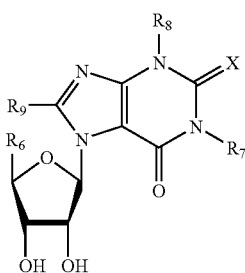

(V)

wherein:
X is or S;
$R_6$ is $R^aR^bNC(=O)—$ or $HOR^c—$, wherein
$R^a$ and $R^b$ may be the same or different and are selected from the group consisting of hydrogen, $C_1–C_{10}$ alkyl, amino, $C_1–C_{10}$ haloalkyl, $C_1–C_{10}$ aminoalkyl, and $C_3–C_{10}$ cycloalkyl, or are joined together to form a heterocyclic ring containing two to five carbon atoms; and
$R^c$ is selected from $C_1–C_{10}$ alkyl, amino, $C_1–C_{10}$ haloalkyl, $C_1–C_{10}$ aminoalkyl, $C_1–C_{10}$ BOC-aminoalkyl and $C_3–C_{10}$ cycloalkyl;
$R_7$ and $R_8$ may be the same or different and are selected from the group consisting of $C_1–C_{10}$ alkyl, $C_1–C_{10}$ cycloalkyl, R- or S-1-phenylethyl, an unsubstituted benzyl or anilide group, and a phenylethyl or benzyl group substituted in one or more positions with a substituent selected from the group consisting of $C_1–C_{10}$ alkyl, amino, halo, $C_1–C_{10}$ haloalkyl, nitro, hydroxyl, acetamido, $C_1–C_{10}$ alkoxy, and sulfonic acid;
$R_9$ is selected from the group consisting of halo, benzyl, phenyl, $C_3–C_{10}$ cylcycloalkyl, and $C_1–C_{10}$ alkoxy; or a salt of such a compound, for example, a triethylammonium salt thereof.

Some of the above defined compounds and their synthesis procedure may be found in detail in U.S. Pat. No. 5,688,774; U.S. Pat. No. 5,773,423, U.S. Pat. No. 6,048,865, WO 95/02604, WO 99/20284 and WO 99/06053, incorporated herein by reference.

More specifically, the following specific examples are specified in U.S. Pat. No. 5,688,774 at column 4, line 67; column 5, line 16; column 5, lines 39–45; column 6, lines 21–42; column 7, lines 1–11; column 7, lines 34–36; and column 7, lines 60–61:

$N^6$ (3-iodobenzyl)-9-methyladenine;
$N^6$-(3-iodobenzyl)-9-hydroxyethyladenine;
R—$N^6$-(3-iodobenzyl)-9-(2,3-dihydroxypropyl) adenine;
S—$N^6$-(3-iodobenzyl)-9-(2,3-dihydroxypropyl) adenine;
$N^6$-(3-iodobenzyladenin-9-yl)acetic acid;
$N^6$-(3-iodobenzyl)-9-(3-cyanopropyl)adenine;
2-chloro-$N^6$-(3-iodobenzyl)-9-methyladenine;
2-amino-N-(3-iodobenzyl)-9-methyladenine;
2-hydrazido-$N^6$-(3-iodobenzyl)-9-methyladenine;
$N^6$-(3-iodobenzyl)-2-methylamino-9-methyladenine;
2-dimethylamino-N-6-(3-iodobenzyl)-9-methyladenine;
$N^6$-(3-iodobenzyl)-9-methyl-2-propylaminoadenine;
2-hexylamino-N-6-(3-iodobenzyl)-9-methyladenine;
$N^6$-(3-iodobenzyl)-2-methoxy-9-methyladenine;
$N^6$-(3-iodobenzyl)-9-methyl-2-methylthioadenine;
$N^6$-(3-iodobenzyl)-9-methyl-2-(4-pyridylthio)adenine;
(1S,2R,3S,4R)-4-(6-amino-2-phenylethylamino-9H-purin-9-yl)cyclopentane-1,2,3-triol;
(1S,2R,3S,4R)-4-(6-amino-2-chloro-9H-purin-9-yl) cyclopentane-1,2,3-triol;

(±)-9-[2α, 3α-dihydroxy-4β-(N-methylcarbamoyl)cyclopent-1β-yl)]-$N^6$-(3-iodobenzyl)-adenine;
2-chloro-9-(2'-amino-2',3'-dideoxy-β-D-5'-methyl-arabinofuronamido)-$N^6$-(3-iodobenzyl)adenine;
2-chloro-9-(2',3'-dideoxy-2'-fluoro-β-D-5'-methyl-arabinofuronamido)-$N^6$-(3-iodobenzyl adenine;
9-(2-acetyl-3-deoxy-β-D-5-methyl-ribofuronamido)-2-chloro-$N^6$-(3-iodobenzyl)adenine;
2-chloro-9-(3-deoxy-2-methanesulfonyl-β-D-5-methyl-ribofuronamido)-$N^6$-(3-iodobenzyl)adenine;
2-chloro-9-(3-deoxy-β-D-5-methyl-ribofuronamido)-$N^6$-(3-iodobenzyl)adenine;
2-chloro-9-(3,5-1,1,3,3-tetraisopropyldisiloxyl-β-D-5-ribofuranosyl)-$N^6$-(3-iodobenzyl)adenine;
2-chloro-9-(2',3'-O-thiocarbonyl-β-D-5-methyl-ribofuronamido)-$N^6$-(3-iodobenzyl) adenine;
9-(2-phenoxythiocarbonyl-3-deoxy-β-D-5-methyl-ribofuronamido)-2-chloro-$N^6$-(3-iodobenzyl)adenine;
1-(6-benzylamino-9H-purin-9-yl)-1-deoxy-N,4-dimethyl-β-D-ribofuranosiduronamide;
2-chloro-9-(2,3-dideoxy-β-D-5-methyl-ribofuronamido)-$N^6$-benzyladenine;
2-chloro-9-(2'-azido-2',3'-dideoxy-β-D-5'-methyl-arabinofuronamido)-$N^6$-benzyladenne;
2-chloro-9-(β-D-erythrofuranoside)-$N^6$-(3- iodobenzyl)adenine;
$N^6$-(benzodioxanemethyl)adenosine;
1-(6-furfurylamino-9H-purin-9-yl)-1-deoxy-N-methyl-62-D-ribofuranosiduronamide;
$N^6$-[3-(L-prolylamino)benzyl]adenosine-5'-N-methyluronamide;
$N^6$-[3-(β-alanylamino)benzyl]adenosine-5'-N-methyluronamide;
$N^6$-[3-(N—T-Boc-β-alanylamino)benzyl]adenosine-5'-N-methyluronamide
6-(N'-phenylhydrazinyl)purine-9-β-ribofuranoside-5'-N-methyluronamide;
6-(O-phenylhydroxylamino)purine-9-β-ribofuranoside-5'-N-methyluronamide;
9-(β-D-2',3'-dideoxyerythrofuranosyl)-$N^6$-[(3-β-(alanylamino)benzyl]adenosine;
9-(β-D-erythrofuranoside)-2-methylamino-$N^6$-(3-iodobenzyl)adenine;
2-chloro-N-(3-iodobenzyl)-9-(2-tetrahydrofuryl)-9H-purin-6-amine;
2-chloro-(2'-deoxy-6'-thio-L-arabinosyl)adenine; and
2-chloro-(6'-thio-L-arabinosyl)adenine.

In U.S. Pat. No. 5,773,423 at column 6, line 39, to column 7, line 14, preferred compounds include those of the formula:

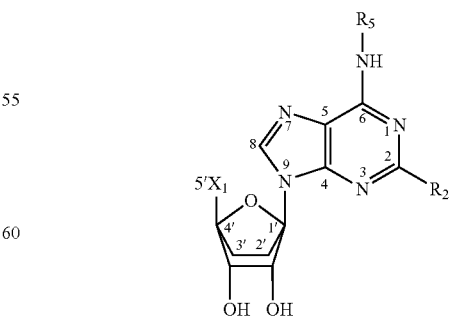

wherein $X_1$ is $R^aR^bNC(=O)$, wherein $R^a$ and $R^b$ may be the same or different and are selected from the group consisting of hydrogen, $C_1–C_{10}$ alkyl, amino, $C_1–C_{10}$ haloalkyl, $C_1–C_{10}$ aminoalkyl, and $C_3$–$C_{10}$ cycloalkyl, $R_2$ is selected from the group consisting of hydrogen, halo, $C_1$–$C_{10}$ alkyoxy, amino, $C_2$–$C_{10}$ alkenyl, and $C_2$–$C_{10}$ alkynyl, and $R_5$ is selected from the group consisting of R- and S-1-phenylethyl, an unsubstituted benzyl group, and a benzyl group substituted in one or more positions with a substituent selected from the group consisting of $C_1$–$C_{10}$ alkyl, amino, halo, $C_1$–$C_{10}$ haloalkyl, nitro, hydroxy, acetamido, $C_1$–$C_{10}$ alkoxy, and sulfo. More preferred compounds include those of the above formula wherein $R^a$ and $R^b$ may be the same or different and are selected from the group consisting of hydrogen and $C_1$–$C_{10}$ alkyl, particularly when $R_2$ is hydrogen or halo, especially hydrogen. Additional preferred compounds are those compounds wherein $R^a$ is hydrogen and $R_2$ is hydrogen, particularly when $R_5$ is unsubstituted benzyl. More preferred compounds are such compounds wherein $R^b$ is a $C_1$–$C_{10}$ alkyl or $C_3$–$c_{10}$ cycloalkyl, particularly a $C_1$–$C_{10}$ alkyl, and more particularly methyl. Especially preferred are those compounds where $R^a$ is hydrogen, $R^b$ is $C_1$–$C_{10}$ alkyl or $C_3$–$C_{10}$ cycloalkyl, and $R_5$ is R- or S-1-phenylethyl or a benzyl substituted in one or more positions with a substituent selected from the group consisting of halo, amino, acetamido, $C_1$–$C_{10}$ haloalkyl, and sulfo, where the sulfo derivative is a salt, such as a triethylammonium salt. An example of an especially preferred compound is IB-MECA. In addition, those compounds in which $R_2$ is a $C_2$–$C_{10}$ alkyne of the formula $R^d$—C≡C— where $R^d$ is a $C_1$–$C_8$ alkyl are particularly preferred. Also preferred are those compounds wherein $R_2$ is other than hydrogen, particularly those wherein $R_2$ is halo, $C_1$–$C_{10}$ alkylamino, or $C_1$–$C_{10}$ alkylthio, and, more preferably, when additionally $R^a$ is hydrogen, $R^b$ is a $C_1$–$C_{10}$ alkyl, and/or $R_5$ is a substituted benzyl. Such preferred compounds include 2-chloro-$N^6$-(3-iodobenzyl)-9-[5-(methylamido)-β-D-ribofuranosyl]-adenine, $N^6$-(3-iodobenzyl)-2-methylamino-9-[5-(methylamido)-β-D-ribofuranosyl]-adenine, and $N^6$-(3-iodobenzyl)-2-methylthio-9-[5-(methylamido)-β-D-ribofuranosyl]-adenine.

Additional preferred compounds are specified in U.S. Pat. No. 5,773,423 at column 7, line 60, through column 8, line 6, as modified xanthine-7-ribosides having the formula:

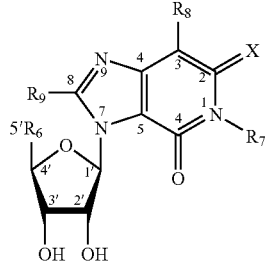

Particularly preferred are those compounds wherein X is O, $R_6$ is $R^aR^bNC(=)$, wherein $R^a$ and $R^b$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, and $C_3$–$C_{10}$ cycloalkyl, $R_7$ and $R_8$ may be the same or different and are selected from the group consisting of $C_1$–$C_{10}$ alkyl, R- and S-1- phenylethyl, an unsubstituted benzyl group, and a benzyl group substituted in one or more positions with a substituent selected from the group consisting of $C_1$–$C_{10}$ alkyl, amino, halo, $C_1$–$C_{10}$ haloalkyl, nitro, hydroxy, acetamido, $C_1$–$C_{10}$ alkoxy, and sulfo, and $R_9$ is selected from the group consisting of halo, benzyl, phenyl, and $C_3$–$C_{10}$ cycloalkyl.

WO 99/06053 discloses in examples 19–33 and originally filed claim 13, compounds selected from the group consisting of:

$N^6$-(4-biphenyl-carbonylamino)-adenosine-5'-N-ethyluronamide;
$N^6$-(2,4-dichlorobenzyl-carbonylamino)-adenosine-5'-N-ethyluronamide;
$N^6$-(4-methoxyphenyl-carbonylamino)-adenosine-5'-N-ethyluronamide;
$N^6$-(4-chlorophenyl-carbonylamino)-adenosine-5'-N-ethyluronamide;
$N^6$-(phenyl-carbonylamino)-adenosine-5'-N-ethyluronamide;
$N^6$-(benzylcarbamoylamino)-adenosine-5'-N-ethyluronamide;
$N^6$-(4-sulfonamido-phenylcarbamoyl)-adenosine-5'-N-ethyluronamide;
$N^6$-(4-acetyl-phenylcarbamoyl)-adenosine-5'-N-ethyluronamide;
$N^6$-((R)-α-phenylethylcarbamoyl)-adenosine-5'-N-ethyluronamide;
$N^6$-((S)-α-phenylethylcarbamoyl)-adenosine-5'-N-ethyluronamide;
$N^6$-(5-methyl-isoxazol-3-yl-carbamoyl)-adenosine-5'-N-ethyluronamide;
$N^6$-(1,3,4-thiadiazol-2-yl-carbamoyl)-adenosine-5'-N-ethyluronamide;
$N^6$-(4-n-propoxy-phenylcarbamoyl)-adenosine-5'-N-ethyluronamide;
$N^6$-bis-(4-nitrophenylcarbamoyl)-adenosine-5'-N-ethyluronamide; and
$N^6$-bis-(5-chloro-pyridin-2-yl-carbamoyl)-adenosine-5'-N-ethyluronamide.

The active ingredient in the case of the GSF-inducing embodiment may also be an A1RAg. It is typically an adenosine derivative having the following formula

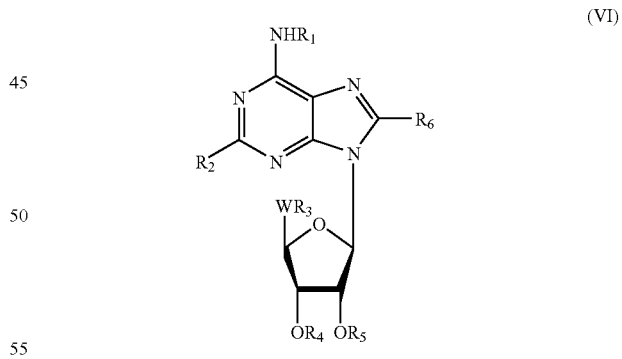

$R_1$ represents a lower alkyl, cycloalkyl, preferably $C_3$–$C_8$ cycloalkyl (including the well known cyclohexyl and cyclopentyl containing derivatives, recognized as CPA and CHA, respectively), the cycloalkyl group may be substituted with, for example, a hydroxyl or lower alkyl; $R_1$ also represents a hydroxyl or hydroxyalkyl; a phenyl, anilide, or lower alkyl phenyl, all optionally substituted by one or more substituents, for example, halogen, lower alkyl, haloalkyl such as trifluoromethyl, nitro, cyano, —$(CH_2)_mCO_2R^a$, —$(CH_2)_mCONR_2R^aR^b$, —$(CH_2)_mCOR^a$, m representing an integer from 0 to 6;

—SOR$^c$, —SO$_2$R$^c$, —SO$_3$H, —SO$_2$NR$^a$R$^b$, —OR$^a$, —SR$^a$, —NHSO$_2$R$^c$, —NHCOR$^a$, —NR$^a$R$^b$ or NHR$^a$CO$_2$R$^b$; wherein R$^a$ and R$^b$ represent independently a hydrogen, lower alkyl, alkanoyl, phenyl or naphthyl (the latter may be partially saturated) the alkyl group optionally being substituted with a substituted or unsubstituted phenyl or phenoxy group; or when R$_1$ represents —NR$^a$R$^b$, said R$^a$ and R$^b$ form together with the nitrogen atom a 5- or 6-membered heterocyclic ring optionally containing a second heteroatom selected from oxygen or nitrogen, which second nitrogen heteroatom may optionally be further substituted by hydrogen or lower alkyl; or —NR$^a$B$^b$ is a group of general formulae (VII) or (VIII):

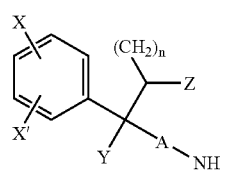
(VII)

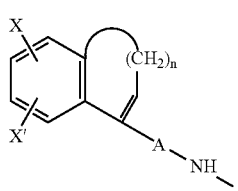
(VIII)

wherein n is an integer from 1 to 4;

Z is hydrogen, lower alkyl or hydroxyl;

Y is hydrogen, lower allyl, or OR' where R' is hydrogen, lower alkyl or lower alkanoyl;

A is a bond or a lower alkylene, preferably, C$_1$–C$_4$ alkenyl; and

X and X' are each independently hydrogen, lower alkyl, lower alkoxy, hydroxy, lower alkanoyl, nitro, haloalkyl such as trifluoromethyl, halogen, amino, mono- or di-lower alkyl amino, or when X and X' are taken together a methylenedioxy group;

R$^c$ represents a lower allyl;

R$_2$ represents a hydrogen; halogen; substituted or unsubstituted lower alkyl or alkenyl group; lower haloalkyl or haloalkenyl; cyano; acetamido; lower alkoxy; lower alkylamino; NR$^d$R$^e$ where R$^d$ and R$^e$ are independently hydrogen, lower alkyl, phenyl or phenyl substituted by lower alkyl, lower alkoxy, halogen or haloalkyl such as trifluoromethyl or alkoxyl; or —SR$^f$ where R$^f$ is hydrogen, lower alkyl, lower alkanoyl, benzoyl or phenyl;

W represents the group —OCH$_2$—, —NHCH$_2$—, —SCH$_2$— or —NH(C=O)—;

R$_3$, R$_4$ and R$_5$ represent independently a hydrogen, lower alkyl or lower alkenyl, branched or unbranched C$_1$–C$_{12}$ alkanoyl, benzoyl or benzoyl substituted by lower alkyl, lower alkoxy, halogen, or R$_4$ and R$_5$ form together a five membered ring optionally substituted by a lower alkyl or alkenyl; R$_3$ further represents independently a phosphate, hydrogen or dihydrogen phosphate, or an alkali metal or ammonium or dialkali or diammonium said thereof;

R$_6$ represents a hydrogen, halogen atom; or one of the R groups (i.e. R$_1$ to R$_6$) is a sulfohydrocarbon radical of the formula R$^g$—SO$_3$—R$^h$—, wherein R$^g$ represents a group selected from C$_1$–C$_{10}$ aliphatic, phenyl and lower allyl substituted aromatic group which may be substituted or unsubstituted and R$^h$ represents a monovalent cation. Suitable monovalent cations include lithium, sodium, potassium, ammonium or trialkyl ammonium, which will enable dissociation to take place under physiological conditions. The remaining R groups being a hydrogen or halogen atom, an unsubstituted hydrocarbon or any other non-sulfur containing group as defined above.

The hydrocarbon chains used herein may include straight or branched chains. In particular, the terms "alkyl" or "alkenyl" as used herein mean a straight or branched chain alkyl or alkenyl groups. The terms "lower alkyl" or "lower alkenyl" mean respectively C$_1$–C$_{10}$ alkyl or C$_2$–C$_{10}$ alkenyl groups and preferably, C$_1$–C$_6$ alkyl and C$_2$–C$_6$ alkenyl groups.

Preferred adenosine derivatives of formula (VI) are the N$^6$-cyclopentyl adenosine (CPA), 2-chloro-CPA (CCPA), and N$^6$-cyclohexyl adenosine (CHA) derivatives, the preparation of which is well known to the person skilled in the art. Other adenosine derivatives which are known to be selective to the A1 receptor are those wherein R$_1$ is an anilide group, the latter may be unsubstituted or substituted for example with hydroxyl, alkyl, alkoxy or with a group —CH$_2$C(O)R''', R''' being an hydroxyl group, —NHCH$_3$, —NHCH$_2$CO$_2$C$_2$H$_5$, (ethyl glycinate), tuloidide (also in which the methyl moiety is replaced with a haloalkyl moiety), or with a group —CH$_2$C(O)NHC$_6$H$_4$CH$_2$C(O)R''', in which R''' represents a group to yield a methyl ester substituent (—OCH$_3$), an amide substituent (e.g. R''' being a group —NHCH$_3$), or R''' being a hydrazide, ethylenediamine, —NHC$_2$H$_5$NHC(O)CH$_3$, 4-(hydroxy-phenyl)propionyl, biotinylated ethylene diamine or any other suitable hydrocarbon which renders the compound an A1 agonist.

Alternatively, the N$^6$-substituted adenosine derivatives used as active ingredients according to the present invention may be those containing an epoxide moiety and more particularly are a cycloalkyl epoxy containing adenosine derivative (e.g. oxabicyclo such as norbornanyl or oxatricyclo such as adamantanyl). Some such compounds may be defined by general formula (I), wherein R$_1$ is a group of general formulae (IXa) and (IXb):

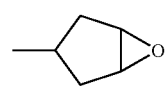
(IXa)

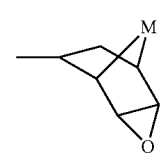
(IXb)

wherein M is a lower alkyl group as defined above.

Embodiments of the agonist compounds having an epoxide N$^6$-norbornyl group include the endo and exo isomers and more particularly, can be one of four isomers: the 2R-exo, 2R-endo, 2S-exo and 2S-endo form.

Another embodiment of the $N^6$-norbornyl derivative may include an oxygen atom at the $N^1$-position of the purine ring. This compound is termed $N^6$-(5,6-epoxynorborn-2-yl)adenosine-1-oxide.

At times, the A1RAg may be an adenine derivative in which the β-D-ribofuranozyl moiety of adenosine is replaced with a hydrogen or phenyl group.

A2RAn, which may be used in accordance with the invention are 8-styryl derivatives of 1,3,7-substituted xanthines of the formula (X):

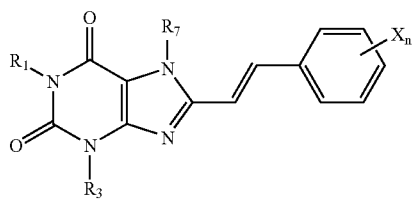

wherein
$R_1$ and $R_3$ are $C_1$–$C_4$ alkyl, allyl or propargyl
$R_7$ is H, methyl or $C_2$–$C_8$ alkyl
n is 1 to 3
and X is a halogen, trifluoroalkyl, alkoxy, hydroxy, nitro, amino, dialkylamino, diazonium, isothiocyanate, benzyloxy, aminoalkoxy, alkoxycarbonylamino, acetoxy, acetylamino, succinylamino, 4-(4-$NH_2$-trans-$CH_2CH=CHCH_2$0-3,5-$(MeO)_2$, 4-(4-AcNH-trans-$CH_2CH=CHCH_2O$)-3,5-$(MeO)_2$, 4-(4-t-BOC-NH-trans-$CH_2CH=CHCH_2O$)-3,5-$(MeO)_2$ A specific example of the compound of formula (X) is (3,7-dimethyl-1-propargyl-xantane).

The A2RAn may also be compounds of the following formulae:

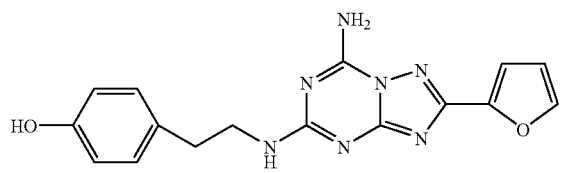

Or,

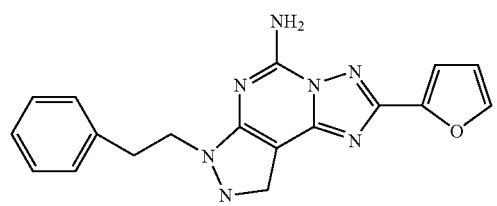

As will be appreciated, the invention may not be limited to the specific A3RAg, A2RAg or A2RAn compounds mentioned above.

The active ingredient in accordance with the invention may be as defined above or may be in the form of salts or solvates thereof, in particular physiologically acceptable salts and solvates thereof. Further, when containing one or more asymmetric carbon atoms, the active ingredient may include isomers and diastereoisomers of the above active ingredients or mixtures thereof.

Pharmaceutically acceptable salts of the above active ingredients include those derived from pharmaceutically acceptable inorganic and organic acids. Examples of suitable acids include hydrochloric, hydrobromic, sulphoric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids.

The active ingredient may be administered as a non-active substance (e.g. pro-drug) and be made active only upon further modification/s by a natural process at a specific site in the subject. In any case, the derivative will be such that the therapeutic functionality of the pharmaceutical composition of the invention, is preserved. Such pro-drugs are also encompassed by the term "active ingredient" as used herein. Similarly, the terms "A3RAg", "A1RAg" "A1RAn" "A2RAg" and "A2RAn" should be understood as encompassing pro-drugs which, although a priori, lack the antagonistic or antagonistic activity (as the case may be), become active in vivo.

The A3RAg in accordance with the invention may be chosen by screening for such compounds which qualitatively have an activity resembling that of IB-MECA. For example, such compounds for use in accordance with the leukopenia-inhibiting embodiment may be screened based on their ability to stimulate proliferation of bone marrow or white blood cells and subsequently based on their ability to exert this activity in vivo. For use in the proliferation-inhibition embodiment, compounds may be screened for their ability to inhibit proliferation of tumor cells as well as subsequently to exert this activity in vivo.

The A1RAn and A2RAn may be tested for their activity and screened for use in therapy in a similar manner, mutatis mutandis, to that described for A3RAg.

The pharmaceutical composition of the invention may comprise the active ingredient as such, but may be combined with other ingredients which may be a pharmaceutically acceptable carrier, diluent, excipient, additive and/or adjuvant, as known to the artisan, e.g., for the purposes of adding flavors, colors, lubrication or the like to the pharmaceutical composition. Evidently, the pharmaceutically acceptable carrier/s, diluent/s, excipient/s, additive/s employed according to the invention generally refer to inert, non-toxic solid or liquid fillers, diluents or encapsulating materials which preferably do not react with the compounds within the composition of the invention.

Further, the active ingredient may also be administered in combination with a chemotherapeutic drug, particularly in the case of the leukopenia prevention embodiment. Thus the pharmaceutical composition according to the invention may comprise, in addition to said active ingredient a chemotherapeutic drug. According to one embodiment of the invention, the chemotherapeutic drug is an anti-cancer chemotherapeutic drug. It should be understood that by the term it is meant any cytotoxic drug or a cocktail comprising a combination of two or more cytotoxic drugs given to a patient for the purpose of reducing the patient's tumor mass.

One finding in accordance with the invention is that the A3RAg is orally bioavailable and exerts its dual activity (reducing abnormal cell proliferation and preventing or reducing leukopenia) when orally administered. Thus, according to one preferred embodiment, the pharmaceutical composition of the invention is formulated for oral administration. Such an oral composition may further comprise a pharmaceutically acceptable carrier, diluent, excipient, additive or adjuvant suitable for oral administration.

Within the scope of the G-CSF-inducing embodiment of the present invention, the pharmaceutical compositions disclosed are particularly used for increasing the level of G-CSF secreted from the cells. Such compositions may be used to accelerate the neutrophil recovery after chemotherapy and bone marrow transplantation or to inhibit abnormal cell growth. To date, such treatments include administration of the growth factor it self, which are known to have undesired side effects. All the more so, the average cost per course of G-CSF therapy is known to be very high.

Within the scope of the leukopenia-prevention embodiment or the toxicity-preventing embodiment of the present invention, the pharmaceutical composition disclosed are particularly used for elevating the level of circulating leukocyte cells in a subject or countering other toxic effects, such as weight loss. This aspect of the invention is applicable in a variety of clinical situations. It is evident that a reduced level of circulating leukocytes and particularly neutrophils may result in a weakened immune system. An example of a weakened immune system which may be treated in accordance with this aspect of the invention, is such which often occurs in advanced stages of cancer or that resulting from drug-induced leukopenia or drug-induced neutropenia.

The proliferation-inhibiting embodiment is useful for the treatment of a variety of abnormalities associated with the abnormal cell growth such as cancer, psoriasis and some autoimmune diseases. In particular, the composition of the invention is employed for inhibiting proliferation of tumor cells, preferably within the framework of anti-cancer therapy.

When treating lymphoma cells with an A3RAg the inhibition of proliferation of these cells was more pronounced than that obtained with adenosine or the 'A1' or 'A2' agonists, although some activity was also observed with the A2RAg (see for example FIG. 5A). These results show that inhibition of tumor cell proliferation should be ascribed mainly to the binding of A3RAg to its corresponding receptor but may also be mimicked to some extent by an A2RAg. The above surprising results thus offers a new therapeutic target for future anti-cancer cytostatic drugs.

A3RAgs were further found to be potent in inhibiting growth of tumor cells, other than lymphoma, e.g. melanoma or colon carcinoma (see for example FIG. 6). A man versed in the art would clearly appreciate the advantage of treating a subject with a non-specific anti-cancer drug capable of inhibiting growth of the abnormally dividing cells while concomitantly being capable restoring the immune system of the subject by inducing bone marrow cell proliferation.

FIGS. 7A–7B, for example, show the differential effect of A3RAg. In this particular case, the effect of IB-MECA, on tumor and normal cells was evaluated. The more pronounced effect obtained using A3RAg, as compared to adenosine, is also clearly presented by these results. The therapeutic effect of A3RAg was reversed when an A3 receptor antagonist, MRS-1220, was employed.

The in vivo studies confirmed the in vitro results which demonstrated a chemoprotective effect of A3RAg on mice which were treated simultaneously with A3RAg and with a cytotoxic agent as compared to mice treated only with the cytotoxic drug (see for example FIG. 8). Further, a decrease in the number of foci in the A3RAg-treated mice was observed indicating the chemotherapeutic activity of A3RAg (see for example FIG. 9). FIGS. 10A–10B as well as 19A and 19B, for example, show that tumor-bearing mice treated only with the cytotoxic drug exhibited a decline in the number of peripheral blood leukocytes and neutrophils, while administration of A3RAg after chemotherapy, resulted in the restoration of the total white blood cell count yielding an increase in the percentage of neutrophils.

Thus, it may be concluded that A3RAg has a dual therapeutic function as it acts both as a chemotherapeutic agent as well as a chemoprotective agent. It is clear that use of A3RAg for this dual effect is also within the scope of the present invention.

In any case, the pharmaceutical compositions of the invention are administered and dosed in accordance with good medical practice, taking into account the clinical condition of the individual patient, the site and method of administration, scheduling of administration, patient's age, sex, body weight and other factors known to medical practitioners.

The composition of the invention may be administered in various ways. It can be administered orally, subcutaneously or parenterally including intravenous, intraarterial, intramuscular, intraperitoneally or by intranasal administration, as well as by intrathecal and infusion techniques known to the man versed in the art.

As known, a treatment course in humans is usually longer than in animals, e.g. mice, as exemplified herein. The treatment has a length proportional to the length of the disease process and active agent effectiveness. The therapeutic regimen involved single doses or multiple doses over a period of several days or more. The treatment generally has a length contingent with the course of the disease process, active agent effectiveness and the patient species being treated.

When administering the compositions of the present invention parenterally, it will generally be formulated in a unit dosage injectable form (solution, suspension, emulsion). The pharmaceutical formulation suitable for injection includes sterile aqueous solutions or dispersions and sterile powders for reconstitution into sterile injectable solutions or dispersions. The carrier employed can be a solvent or dispersing medium containing, for example, water, ethanol, polyol (for example, glycerol, propylene glycol, lipid polyethylene glycol and the like), suitable mixtures thereof and vegetable oils.

Non-aqueous vehicles such as cottonseed oil, sesame oil, olive oil, soybean oil, corn oil, sunflower oil, or peanut oil and ester, such as isopropyl myristate, may also at times be used as solvent systems for the active ingredient.

Additionally, various additives which enhance the stability, sterility and isotonicity of the compositions, including antimicrobial preservatives, antioxidants, chelating agents and buffers can be added. Prevention of the action of microorganisms can be ensured by various antibacterial and antifungal agents, for example, parabens, chlorobutanol, phenol, sorbic acid and the like.

For the purpose of oral administration, the active ingredient may be formulated in the form of tablets, suspensions, solutions, emulsions, capsules, powders, syrups and the like, are usable and may be obtained by techniques well known to the pharmacists.

The present invention is defined by the claims, the contents of which are to be read as included within the disclosure of the specification, and will now be described by way of example with reference to the accompanying Figures. It is to be understood, that the terminology which has been used is intended to be in the nature of words of description rather than limitation.

While the foregoing description describes in detail only a few specific embodiments of the invention, it will be understood by those skilled in the art that the invention is not limited thereto and that other variations in form and details may be possible without departing from the scope and spirit of the invention herein disclosed.

BRIEF DESCRIPTION OF THE FIGURES

In order to understand the invention and to see how it may be carried out in practice, a preferred embodiment will now be described, by way of non-limiting example only, with reference to the accompanying drawings, in which:

FIG. 12A shows the white blood cell (WBC) count while FIG. 12B shows the count of bone marrow nucleated cells. In FIG. 12A results are shown for the two different treatments at four different time periods, with the control level being indicated by a dashed line, while in FIG. 12B, the results at two different time periods are shown with the control level being represented by a bar at the left hand side.

EXPERIMENTAL RESULTS

Tumor Cells

Figure 1:
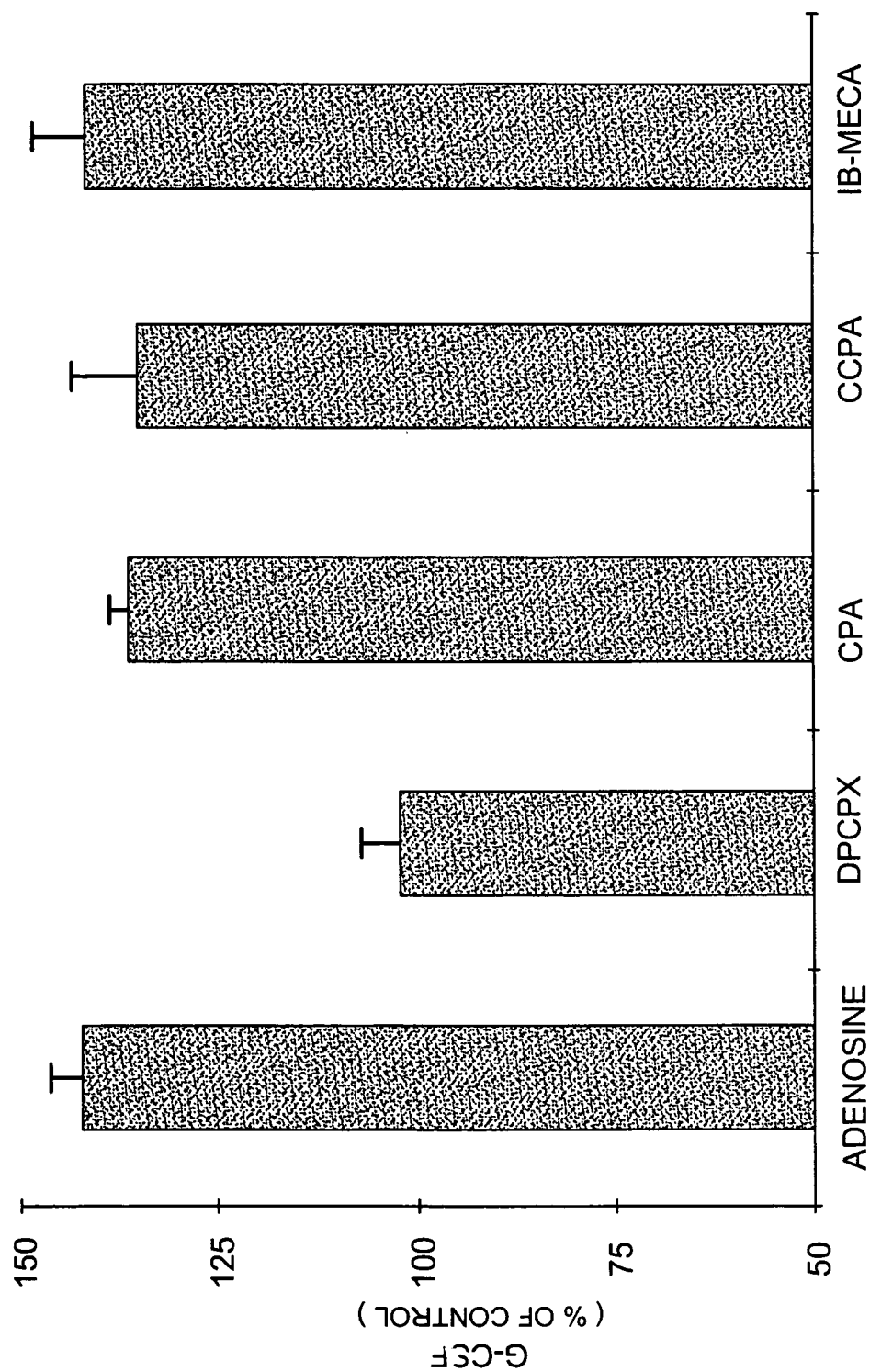
FIG. 1 is a bar graph showing results of an in vitro assay in which the effect of adenosine (Ad), DPCPX (an A1RAn), CPA and CCPA (both A1RAg) or IB-MECA (an A3RAg) on G-CSF production is shown. Cultures treated with modified RPMI served as the control. The results are presented in terms of percent of control (control=100%).

Murine tumor cell lines (B-16 melanoma and Nb2 11c rat Lymphoma) were used. B-16 melanoma cells were obtained from the American Type Tissue Culture Collection (ATCC), Rockville, Md. Nb2-11C rat lymphoma cells [Pines M., and Gertler A. *J. of Cellular Biochem.*, 37:119–129 (1988)] was kindly provided by Dr. A. Gertler, Hebrew university, Israel.

Colon carcinoma cells (HCT-116) were also employed and were obtained at the ATCC.

The cells were routinely maintained in RPMI medium containing 10% fetal bovine serum (FBS, Biological Industries, Beit Haemek, Israel). Twice a week the cells were transferred to a freshly prepared medium.

Normal Cells

Bone marrow cells derived from the femur of C57BL/6J mice were used. The cells were prepared as previously described [17].

Drugs/Compounds

The drugs employed were: adenosine; adenosine A1 receptor agonists: CCPA [2-chloro-N$^6$-cyclopentyl-adenosine], CPA (N-cyclopentyladenosine); A1RAn: DPCPX (1,3-dipropyl-8-cyclopentylxanthine); adenosine A2 receptor agonist: DMPA (N$^6$-[2-(3,5-dimethoxyphenyl)-2-(2-methylphenyl)-ethyl] adenosine) A2RAn: DMPX (3,7-dimethyl-1-propargyl-xantane); A3RAg: IB-MECA (1-deoxy-1-{6-[({3-iodophenyl}methyl)amino]-9H-purine-9-yl}-N-methyl-β-D-ribofuranuronamide)), CE-IB-MECA (2-chloro-N$^6$-3-iodobenzyl)-adenosine-5'-N-methyl-uronamide; and adenosine A3 receptor antagonist: MRS-1523 (5-propyl-2-ethyl-4-propyl-3-ethylsulfanylcarbonyl)-6-phenylpyridine-5-carboxylate) and MRS-1200 (9-chloro-2-(2-furanyl)-5-[(phenylacetyl)amino] [1,2,4,]-triazolo[1,5-c]quinazoline).

Anti-murine G-CSF antibodies (rabbit antiserum purified by protein A chromatography, Cytolab LTD, Weizmann Institute of Science, Israel) were used.

Cyclophosphamide was purchased from Taro Pharmaceutical Industries Ltd. Haifa Bay, Israel.

Mice

Female ICR, C57BL/6J or mice (BALB/C origin) mice aged 3 months, weighing an average of 25 g were used. The mice were purchased from Harlan Laboratories, Jerusalem, ISRAEL. Standarized pelleted diet and tap water were supplied.

EXAMPLE 1

Effect of Adenosine and Adenosine Receptor Antagonists and Agonists on G-CSF Production and Bone Marrow Cell Proliferation To test the assumption that adenosine exerts its biological effect through stimulation of G-CSF production, normal cells were cultured in the presence adenosine or an adenosine agonist or antagonist.

For this purpose, bone marrow cells obtained from the femur of C57BL/6J or ICR mice were first disaggregated by passing through a 25 G needle. Then, the cells (3×10$^5$ cells/well, in 96 microtiter plates) were incubated with RPMI medium containing 10% fetal bovine serum (FBS) in the presence of adenosine (25 µM). Adenosine or agonists to the A1 and A3 adenosine receptors—CPA (an A1RAg, 0.01 µM), CCPA (an A1RAg, 0.01 µM), or IB-MECA (an A3RAg, 0.01 µM), were added to the bone marrow cultures in the absence of adenosine; an A1 adenosine receptor antagonist, DPCPX (0.1 µM), was added to a bone marrow culture in the presence of adenosine (25 µM).

Cultures containing cells suspended in RPMI medium and 5% FBS served as the control for the above detailed experiment.

[$^3$H]-Thymidine incorporation assay was used to evaluate the proliferation of the bone marrow cells. For this purpose, after 30 hours of incubation, each well was pulsed with 1 µCi [$^3$H]-Thymidine. After a total of 48 hours of incubation, the cells were harvested and the [$^3$H]-Thymidine uptake was determined in an LKB liquid scintillation counter (LKB, Piscataway, N.J., USA). The results of this assay are depicted in FIG. 1 which shows that A1RAg or A3RAg have an effect on the production of G-CSF, that is similar to that obtained with adenosine.

Figure 2:
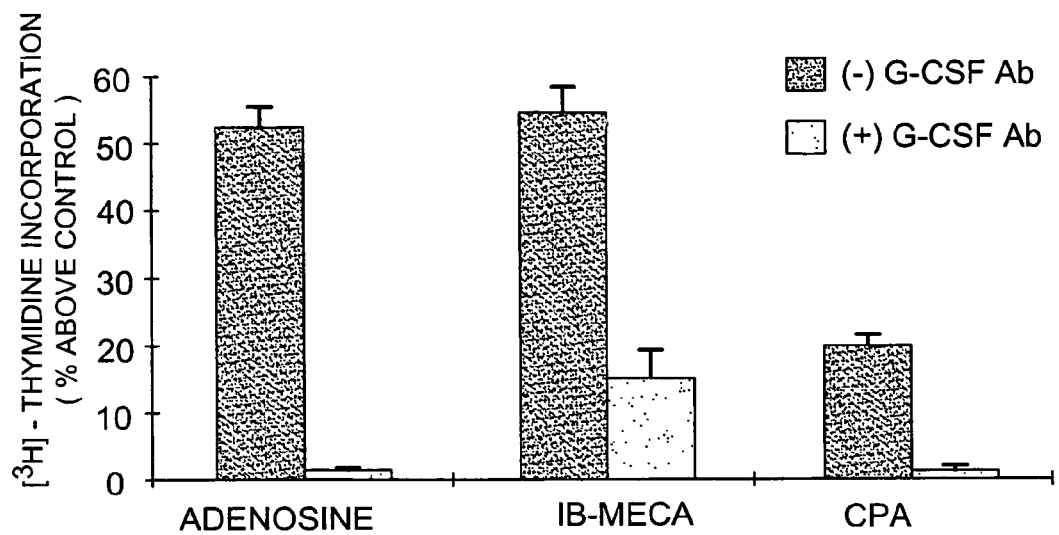
FIG. 2 is a bar graph showing results, obtained by [$^3$]-thymidine incorporation assay, of an experiment in which stimulation of proliferation of bone marrow cells by either adenosine, CPA or IB-MECA, with ((+) G-CSF Ab—light-colored columns) or without antibodies against G-CSF ((−) G-CSF Ab—dark columns) was tested. The results show the neutralization effect of the anti-g-CSF antibodies. The results are represented in terms of percent increase over control (control=0%).
Figure 4:
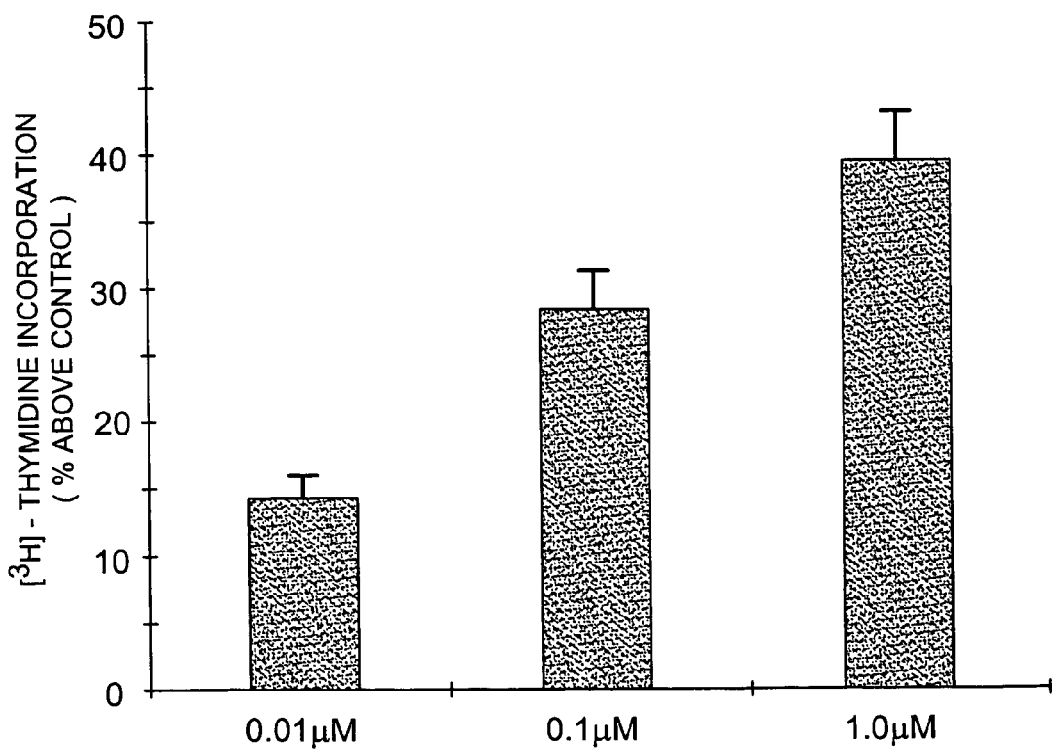
FIG. 4 is a bar graph showing results of an in vitro experiment in which the proliferation of bone marrow cells under three different concentrations of IB-MECA (0.01 μM, 0.1 μM and 1.0 μM) was tested. These results are presented in terms of the [$^3$H]-thymidine incorporation—percent above control (control 0%). The numbers below the bars are the IB-MCA concentrations (μM).

To confirm that adenosine and its agonists exert their effect via stimulation of G-CSF production, a further assay was conducted where anti-G-CSF antibodies (62.5 ng/ml) were added to a culture of bone marrow cells in the presence of adenosine (25 µM), CPA (0.01 µM) or IB-MECA (0.01 µM). Cell proliferation was evaluated as described above. The results of this experiment are depicted in FIG. 2 which shows that antibodies to G-CSF inhibited the stimulatory effect of adenosine and its agonists on the proliferation of bone marrow cells. These results suggest that at least some of the activities associated with interaction with adenosine receptors is mediated through the induction of G-CSF.

Figure 3A:
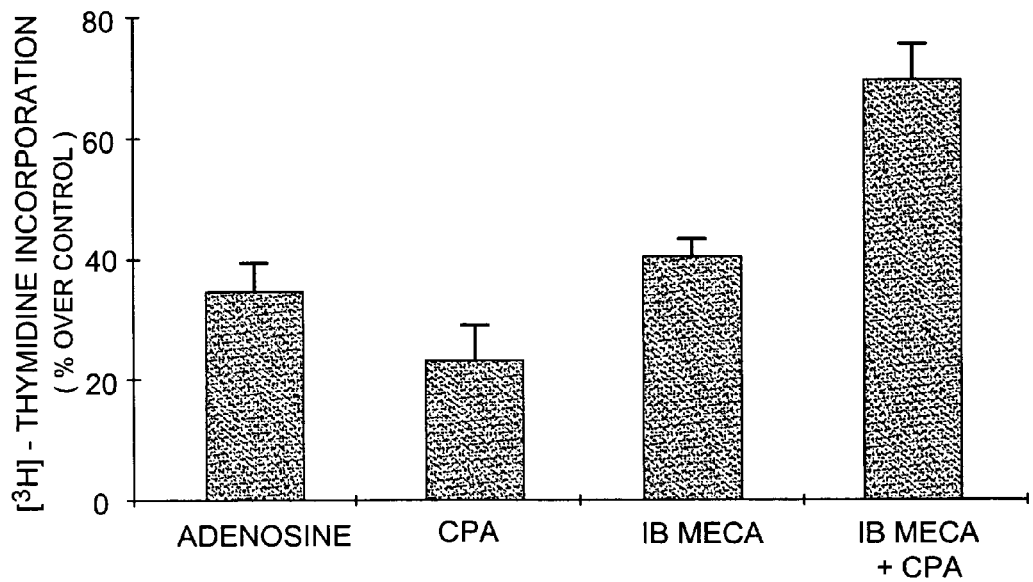
FIGS. 3A and 3B are two bar graphs showing results, obtained by a [$^3$H]-thymidine incorporation assay, of an experiment, in which proliferation of bone marrow cells was tested in the presence of adenosine, an adenosine receptor agonists (FIG. 3A) or adenosine in combination with an adenosine receptor antagonists (FIG. 3B). The receptor agonists tested (FIG. 3A) are CPA (an A1RAg) and IB-MECA (an A3RAg); the receptor antagonists tested (FIG. 3B) were DPCPX (an A1RAn), DMPX (an A2RAn) and MRS (an A3RAn). The results are presented in terms of percent increase in thymidine incorporation over control (control=0%).

The cumulative effect on the proliferation of bone marrow cells, when using a combination of an A1RAgm1 A3RAg, (CPA and IB-MECA) was evaluated. The assay was carried out similarly to that of the experiment the results of which are shown in FIG. 1. Cells, after being disaggregated, were incubated in the presence of either adenosine (25 μM), CPA (0.01 μM), IB-MECA (0.01 μM) or a combination of IB-MECA and CPA (each in a concentration of 0.01 μM) and further treated as described above. The results are depicted in FIG. 3A which shows increased combined effect of IB-MECA and CPA.

Figure 3B:
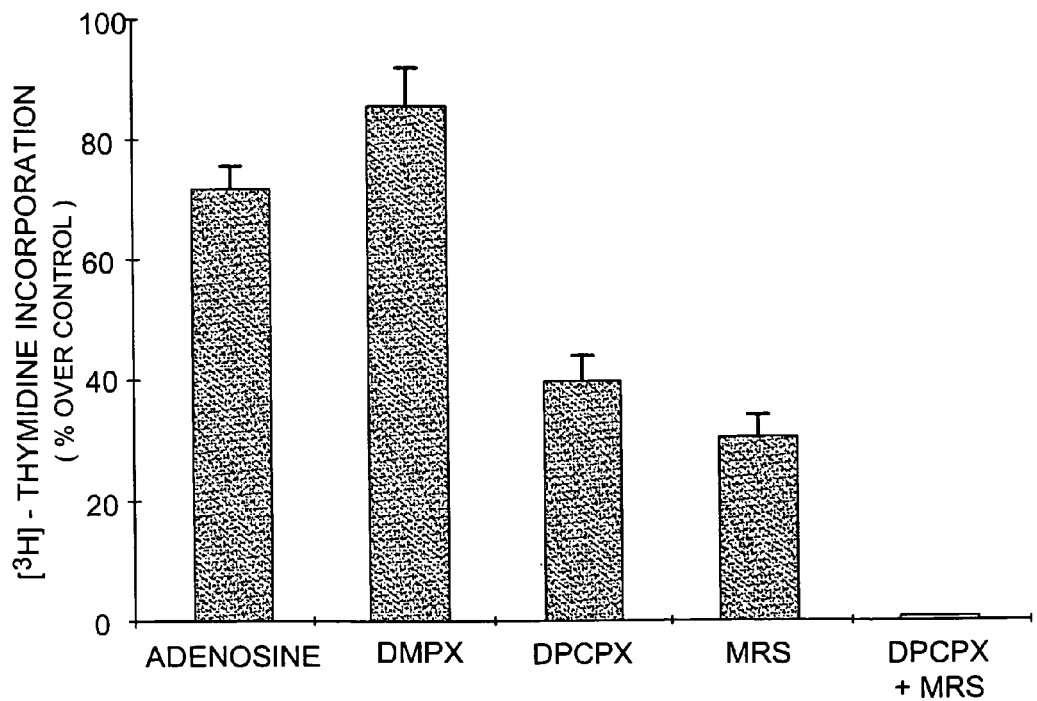

In order to compare the effect of adenosine receptor antagonist on the proliferation of bone marrow cells, following the same methodology described above, cells were incubated with adenosine alone or in combination with either DMPX (an A2RAn), DPCPX (an A1RAn), MRS-1220 (an A3RAn) or with a combination of DPCPX and MRS-1220. The results are shown in FIG. 3B. As can be seen, blocking the A2 receptor by DMPX also resulted in an increased proliferation of bone marrow cells which even exceeded that of adenosine alone. In comparison, proliferation with DPCPX or MRS-1220, reduced the increase by about 50% as compared to adenosine alone, while DPCPX in combination with MRS-1220 inhibited proliferation altogether.

Cells pre-treated as described above, were incubated at different concentrations of IB-MECA (1 μM, 0.1 μM or 0.01 μM). The percent of stimulation was determined by [$^3$H]-Thymidine incorporation assay and the results are depicted in FIG. 3 which show that IB-MECA stimulates proliferation of bone marrow in a dose dependent manner.

EXAMPLE 2

Modulation of Tumor Cell Growth by Adenosine and its Agonists

Nb2-11C rat lymphoma cells (1.2×10$^4$ cells/ml) were incubated for 48 hours in 96 well microtiter plates with 1 ml RPMI medium containing 5% fetal bovine serum. Either 25 μM adenosine, 0.01 μM of an adenosine receptor agonists (CPA, an A1RAg; DPMA, an A2RAg or IB-MECA, an A3RAg) or 0.1 μM of an adenosine receptor antagonists (DPCPX, an A1RAn; DMPX, an A2RAn; or MRS-1220, an A3RAn) in combination with adenosine (25 μM) was added.

Cultures containing cells suspended in RPMI medium with 5% FBS served as controls for the above detailed experiment. Extent of cell proliferation was measured by a cell count assay.

Figure 5A:
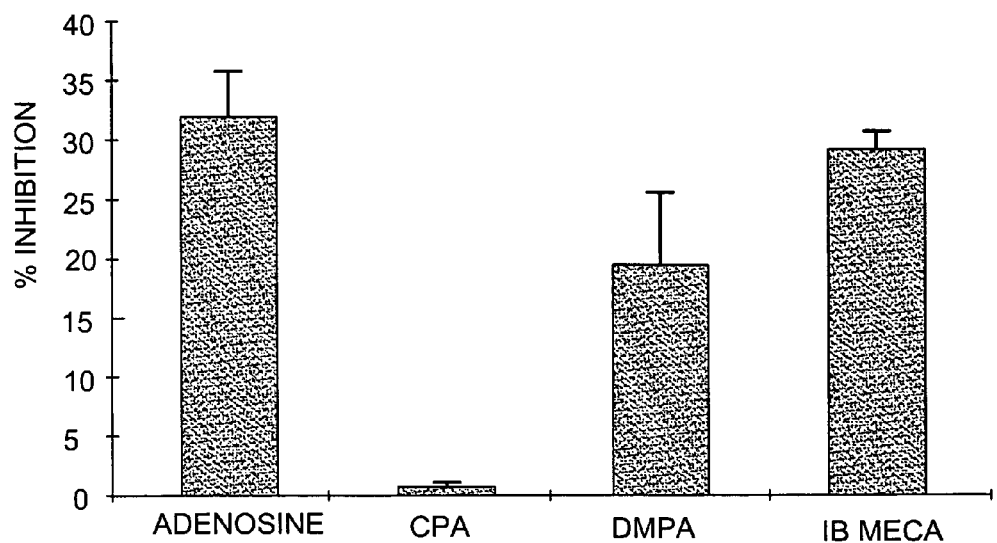
FIGS. 5A and 5B are bar graphs showing results of two experiments, both carried, out in vitro and being based on cell count assays, in which the effect of growth of lymphoma cells (Nb2-11C) by adenosine and its antagonist was tested. In the experiment shown in FIG. 5A, the effect on lymphoma cell growth by adenosine, CPA (an A1RAg), DMPA (an A2RAg) or IB-MECA (an A3RAg) was tested. In the experiment shown in FIG. 5B, the effect on the lymphoma cell growth by adenosine, DPCPX (an A1RAn), DMPX (an A2RAn) or MRS-1220 (an A3RAn) was tested. RPMI-treated lymphoma cells serve as control. The results are depicted as % inhibition of growth over that of control (control=0%).
Figure 5B:
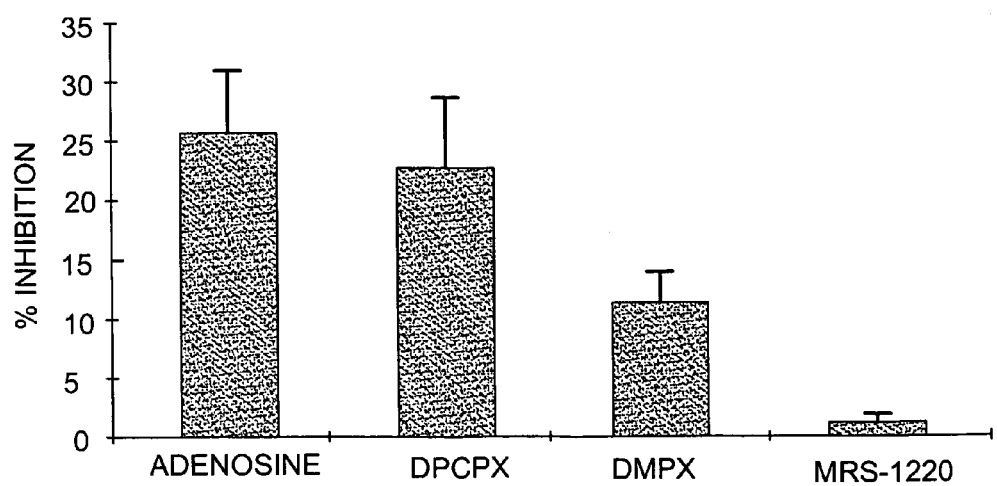

The results are shown in FIGS. 5A and 5B, comparable to the inhibition with adenosine. As can be seen, the proliferation of Nb2-11C cells, was markedly inhibited following incubation with IB-MECA, an A3RAg. No growth inhibition was seen in the presence of CPA, an A1RAg, and a lower growth inhibition was seen in the presence of DPMA, an A2RAn. The failure of CPA to inhibit the proliferation of these two tumor cells, suggested that the adenosine A1 receptor is not involved in this activity. However, the inhibitory activity of both DMPA and IB-MECA suggests the role of the A2 and the A3 adenosine receptors, respectively, in this inhibitory effect.

Further, it can be seen that DPCPX, an A1RAn, had essentially no effect, while in the presence of MRS-1220, an A3RAn, the effect of adenosine on the proliferation of Nb2-11C cells was substantially abolished. A minor, however still significant effect was exerted by DMPX, an A2RAn. These findings lead to the conclusion that tumor cell growth may be effectively inhibited by an A3RAg or an A2RAn.

Figure 6:
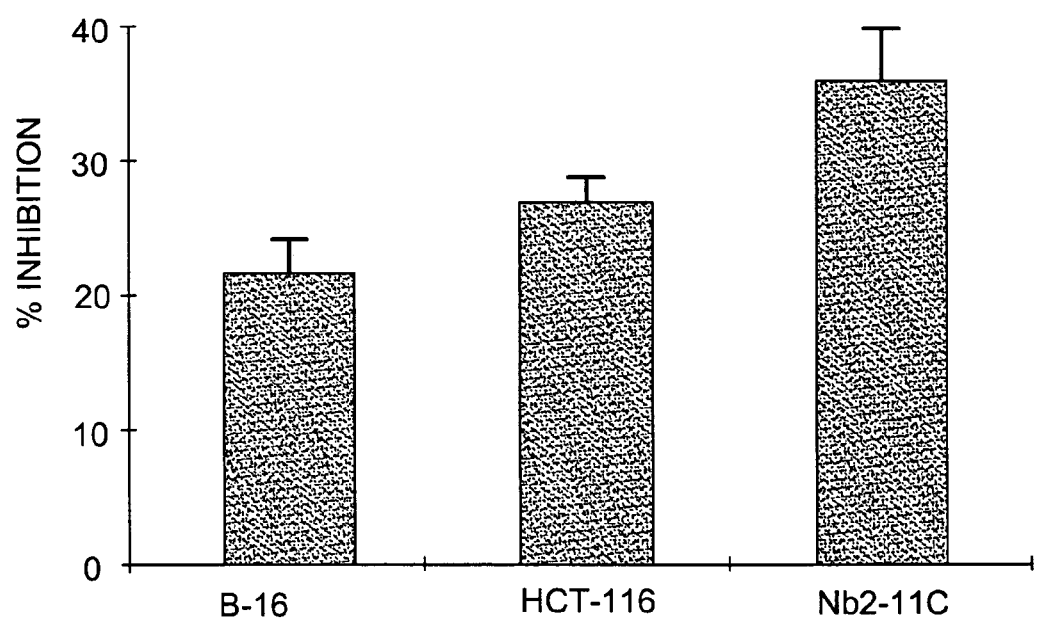
FIG. 6 is a bar graph showing results of an in vitro assay in which growth of different tumor cell types (B16 melanoma, HTC-116 colon carcinoma, Nb2-11C lymphoma) was inhibited in the presence of the A3RAg IB-MECA. RPMI-treated cells served as control. The results are presented as percent inhibition over control (control=0%).

In the same manner as described above, inhibition of growth of B-16 melanoma, HCT-116 colon carcinoma and Nb2-11C lymphoma, by the A3RAg, IB-MECA, was evaluated. The results are shown in FIG. 6 in terms of percent of inhibition or proliferation.

EXAMPLE 3

Adenosine A3 Receptor Agonists Exert a Differential Effect on Tumor and Normal Cells The effect of adenosine, A3RAns and A3RAgs, on the growth of tumor cells was examined, following the experimental procedure described above.

Figure 7A:
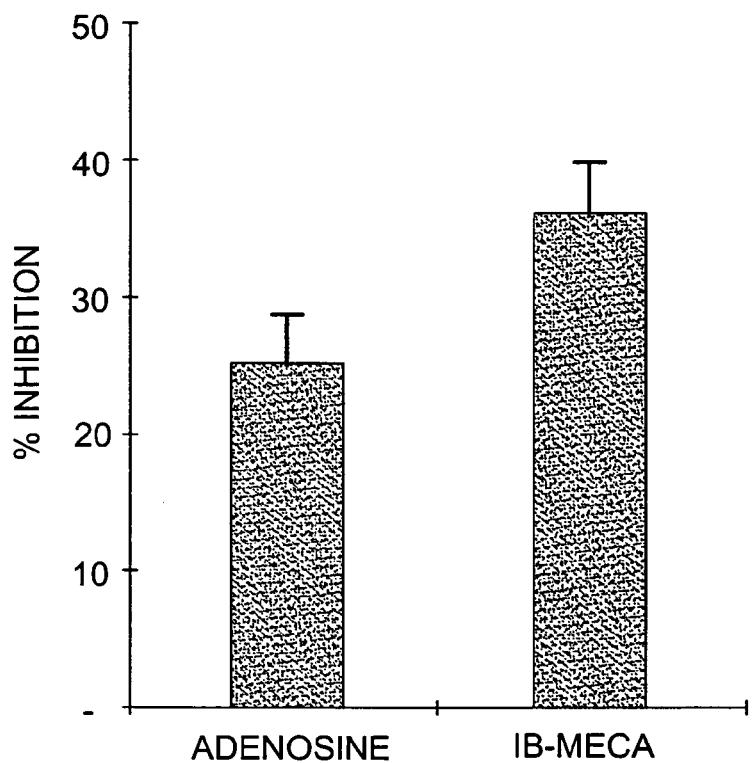
FIGS. 7A and 7B are bar graphs showing the results of an in vitro assay in which the effect of adenosine or the A3RAg, IB-MECA on growth of tumor cells (Nb2-11C Lymphoma, FIG. 7A) or bone marrow cells (FIG. 7B was tested). The results in FIGS. 7A and 7B are shown in terms of percent inhibition and percent stimulation, respectively, as compared to control (control=0%).
Figure 7B:
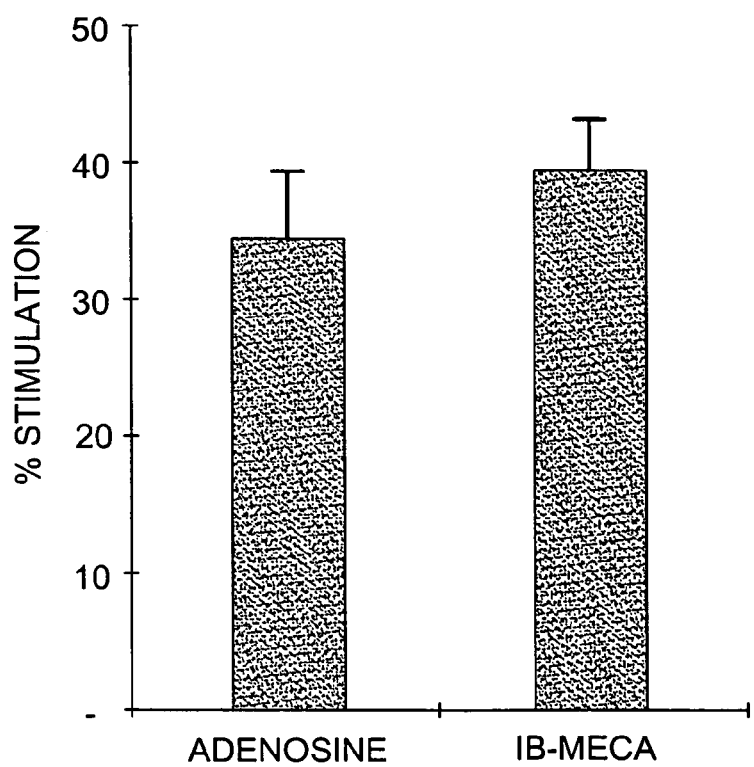

Briefly, Nb2-11C lymphoma or bone marrow cells were incubated in the presence of either adenosine, or IB-MECA. The dual effect of A3RAg is inhibiting the growth of tumor cells while stimulating the proliferation of bone marrow cells is depicted FIGS. 7A and 7B.

EXAMPLE 4

In vivo Studies

40 C57BL6/J mice were divided into 4 groups each of which were treated, by one of the following protocols:
1. Control group: daily intraperitoneal (i.p.) injection of 1 ml saline per mouse from day of tumor inoculation until the mice were sacrificed;
2. Chemotherapy group: one i.p. injection of cyclophosphamide 24 hours after inoculation of tumor cells and daily i.p. injection of 1 ml saline per mouse from day of tumor inoculation until the mice were sacrificed.
3. Adenosine A3 receptor agonist (A3RAg) group: daily oral administration of IB-MECA from day of tumor inoculation until the mice were sacrificed.
4. A3RAg+chemotherapy group: one i.p. injection of cyclophosphamide 24 hours after inoculation of tumor cells and daily oral administration of 3 μg/kg body weight of IB-MECA.

Figure 8:
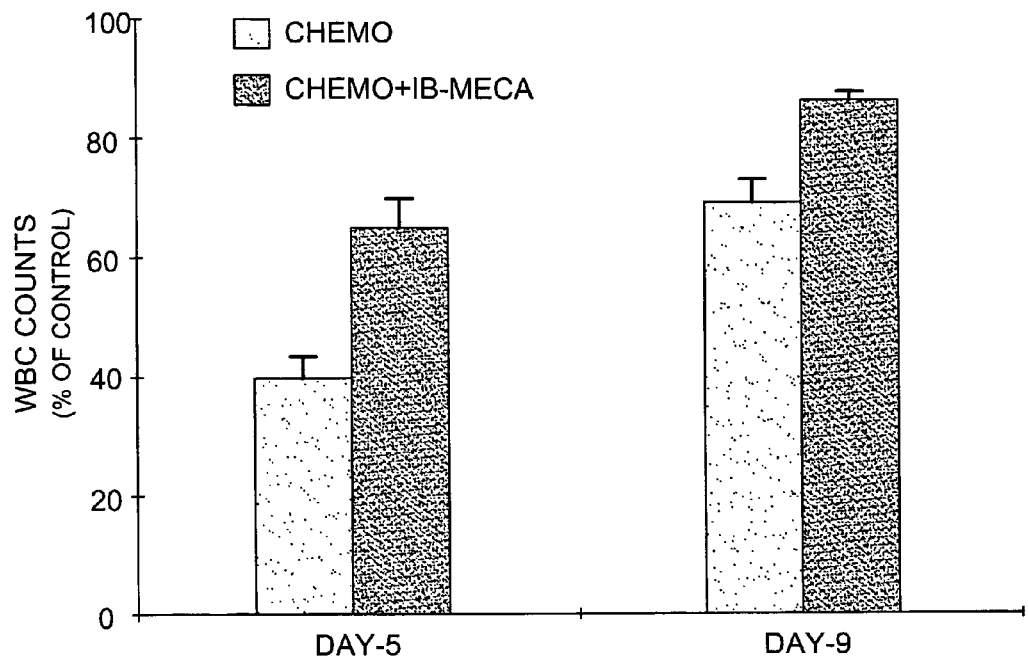
FIG. 8 is a bar graph showing the results of an in vivo experiment where the count of peripheral white blood cells (WBC) after 5 and 9 days of treatment with a chemotherapeutic drug (cyclophosphamide) was tested. The cyclophosphamide was either administered alone (gray columns) or in combination with IB-MECA administered orally (in a 1 ml solution) by daily administration, beginning 24 hours after the chemotherapeutic drug. PBS-treated mice served as control. The WBC count (WBC Counts) is given as percent over control (control=0%).

On day 5 and day 9 the mice were bled from the tail vain and blood samples were obtained for white blood cell (WBC) count. The results are depicted in FIG. 8.

Figure 9:
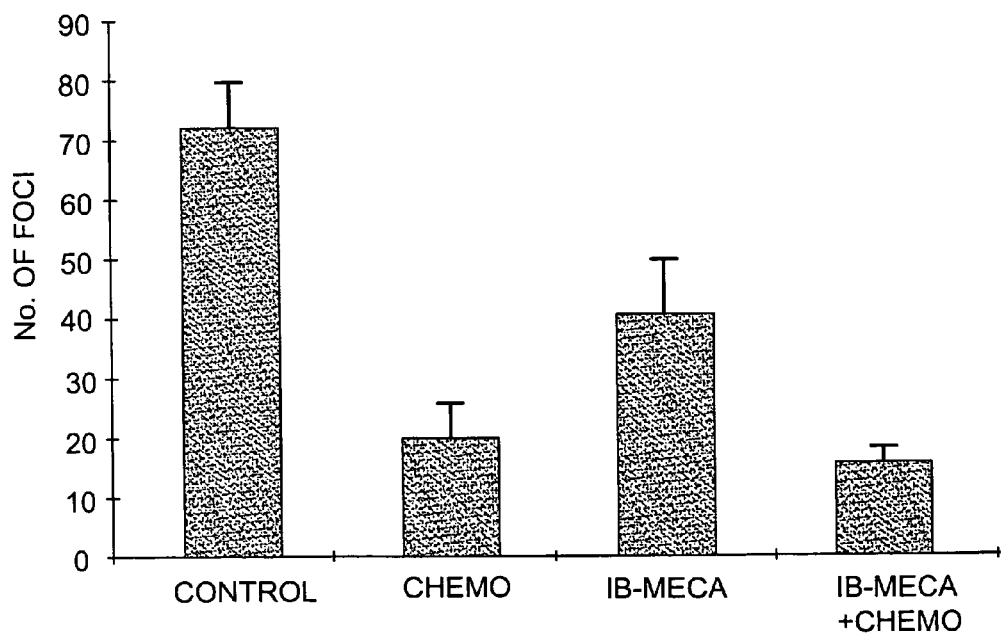
FIG. 9 is a bar graph showing results of an in vivo experiment in which the number of melanoma foci developed in mice following inoculation of 2×10$^5$ melanoma cells into the mice, treated with chemotherapy cyclophosphamide (CHEMO), with IB-MECA, an A3RAg with a combination of IB-MECA and CHEMO or with phosphate buffer saline (PBS) which served as control.

In addition, following 18 days the mice were sacrificed and melanoma tumor foci were counted in the lung. The results are depicted in FIG. 9.

Figure 10A:
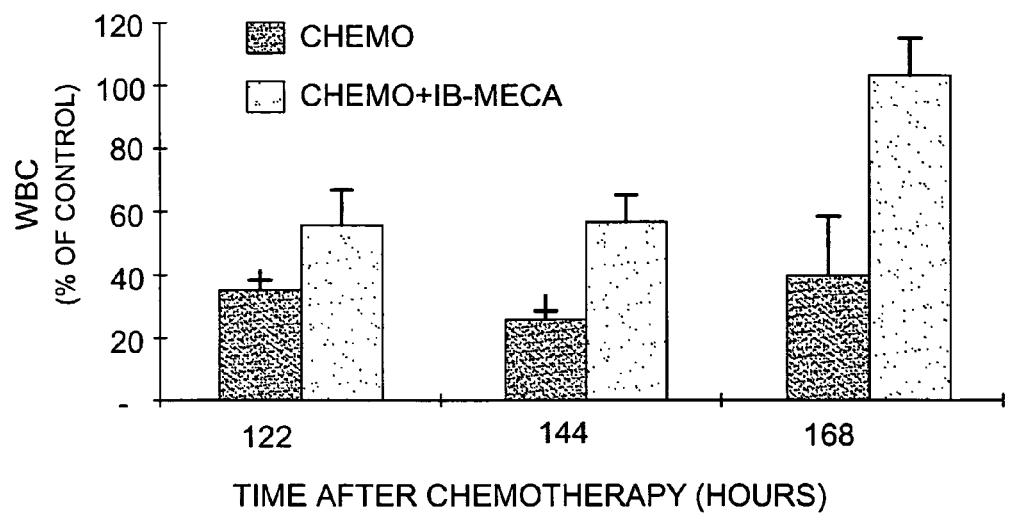
FIGS. 10A and 10B are bar graphs showing the results of in vivo experiment demonstrating the chemotherapeutic activity of IB-MECA. The level of white blood cells (WBC, FIG. 10A) and neutrophils (FIG. 10B) as a function of time (hours after administration) of the chemotherapeutic drug cyclophosphamide (CHEMO) with (CHEMO+IB-MECA) and without IB-MECA administration is shown). Tumor bearing mice treated with PBS served as control. The neutrophil count is shown as % over control (control=0%).
Figure 10B:
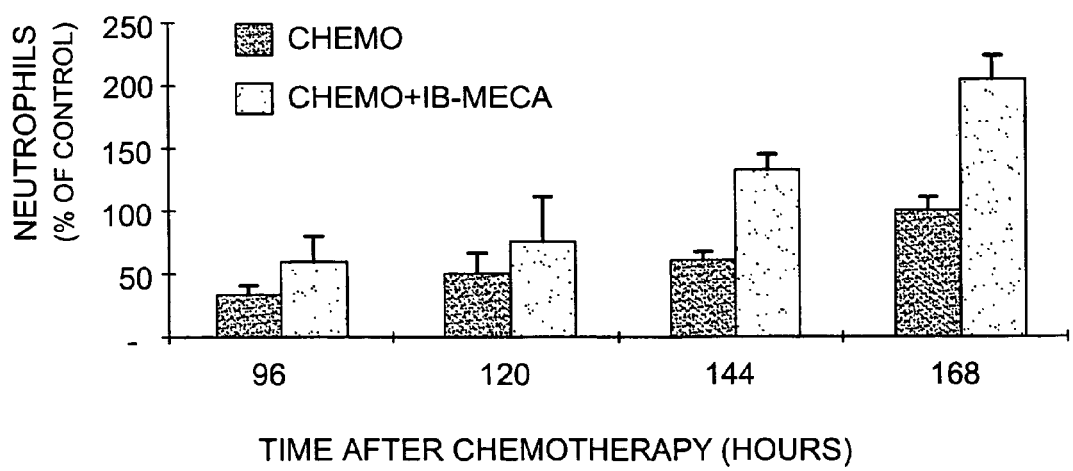

A further experiment was conducted in order to evaluate the chemoprotective effect of A3RAg. Mice were treated with cyclophosphamide (50 mg/kg body weight in 0.3 ml PBS). After 48 and 72 hours from administration of the cytotoxic drug, the mice were injected i.p. with adenosine (25 μg/kg body weight) or with IB-MECA (3 or 6 μg/kg body weight in 0.2 ml PBS). The number of white blood cells (WBC) and neutrophils was tested. The results are shown in FIGS. 10A (WBCs) and 10B (neutrophils), respectively.

As can be seen, mice treated with cyclophosphamide only exhibited a decline in the number of peripheral blood leukocytes and neutrophils as compared to the group treated only with IB-MECA. When adenosine or IB-MECA were administered, the total white blood cell count was restored with the latter having a very pronounced effect, yielding a complete recovery after 168 hours (7 days).

EXAMPLE 5

Adenosine A3 Receptor Agonist Prevents Weight Loss in Mice Treated with a Chemotherapeutic Drug 4 groups of nude mice (BALB/C origin), 10 in each group were treated as follows:
Group 1: The mice were untreated [please confirm].
Group 2: The mice were injected intraperitoneally (i.p.) with 5-fluoro-uracyl (5-FU, 30 mg/kg body weight in PBS) for five consecutive days.
Group 3: The mice were injected i.p. with 5-FU as in Group 2 but starting on day 2, and every second day thereafter, the mice were given an oral administration of Cl-IB-MECA (6 µg/kg body weight, in 0.2 ml PBS.
Group 4: The mice received Cl-IB-MECA, as above.

Figure 11:
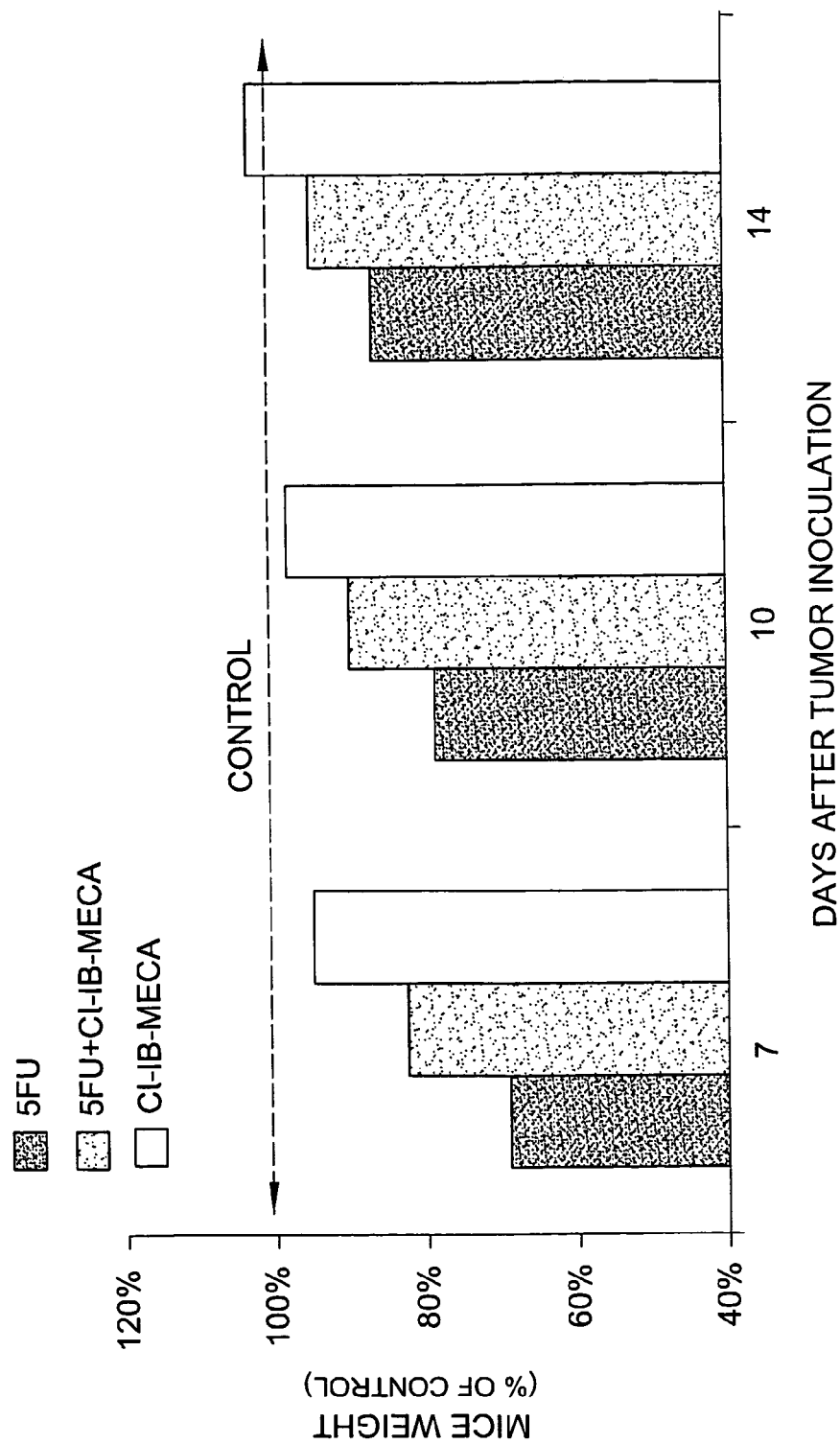
FIG. 11 shows weight of nude mice at 7, 10 and 14 days after onset of treatment (administration of 5-FU, Cl-IB-MECA or a combination of 5-FU and Cl-IB-MECA), as % of control (non-treated mice=100%). The treatments consisted of administration of 5-FU (dark columns), administration of 5-FU in combination with Cl-IB-MECA (an A3RAg)—gray columns) and Cl-IB-MECA alone (white columns).

The mice weight was measured at day 7, 10 and 14. The results are shown in FIG. 11.

As can be seen, 5-FU had a profound effect on the weight of the mice as compared to control, while Cl-IB-MECA administered together with the 5-FU, prevented some of this weight loss. The Cl-IB-MECA by itself did essentially not give rise to any weight loss.

This experiment demonstrates that the A3 adenosine receptor agonists have general protecting effect on some of the toxic effects of chemotherapy.

EXAMPLE 6

Cl-IB-MECA Protects the Mice Against Myelotoxic Effects of the Chemotherapeutic Drug Doxorubicin ICR mice were treated with doxorubicin (injection of 10 mg/kg i.p. in 0.5 ml PBS). After 24, 48 and 72 hours from administration of the cytotoxic drug, the mice were orally administered with Cl-IB-MECA (6 µg/kg body weight). At 72 hours, 96 hours, 120 hours and 144 hours, the mice were sacrificed and blood samples were withdrawn. In addition, bone marrow cells were aspirated from the femur of the mice and a cell count of nucleated cells from this aspirated preparation was made, following staining of the preparation with Coomassie Blue.

Three groups of mice were tested:
Group 1: (control) mice administered with PBS only.
Group 2: Mice treated with doxorubicin only.
Group 3: Administration of doxorubicin as above coupled with administration of Cl-IB-MECA).

Figure 12A:
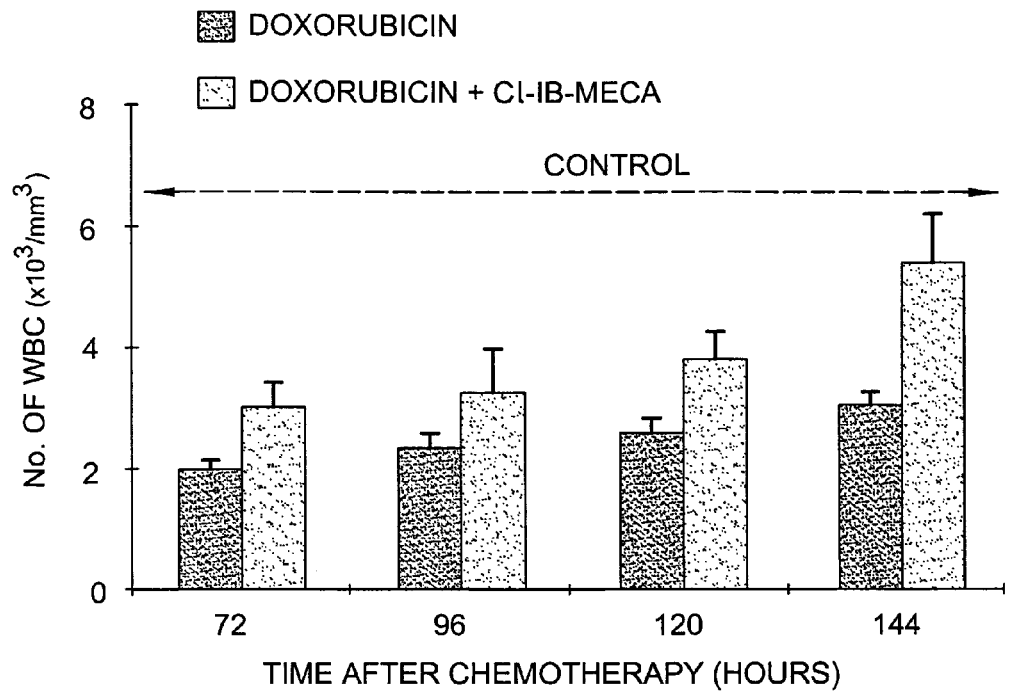
FIGS. 12A and 12B show results of an experiment in which the effect of Cl-IB-MECA in reduction of doxorubicin-induced myelotoxicity was examined. The experiment was performed in ICR mice.
Figure 12B:
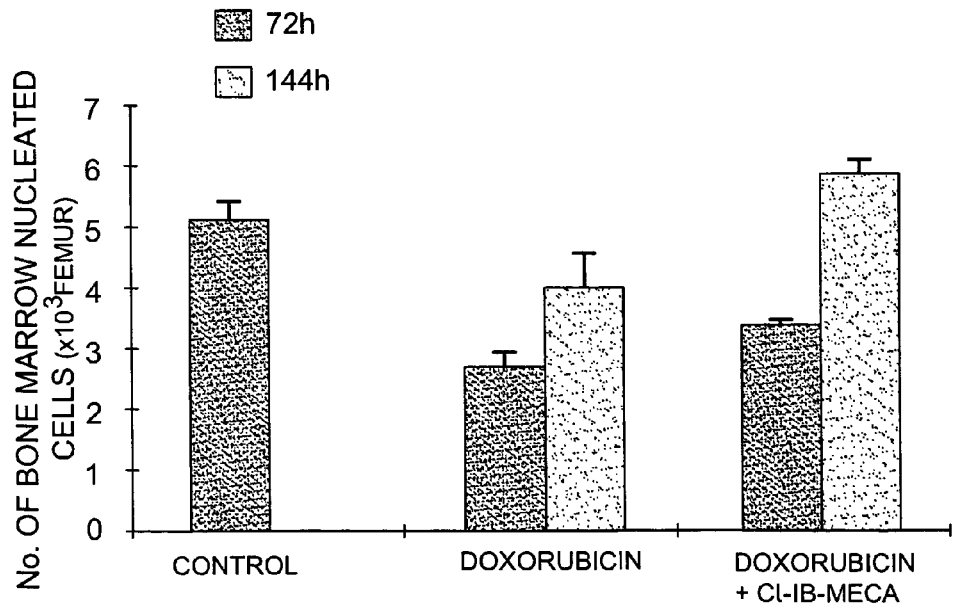

The results of the white blood cell count can be seen in FIG. 12A, and that of the bone marrow nucleated cell count in FIG. 12B. These results clearly show that upon administration of Cl-IB-MECA, there is a marked increase in the number of peripheral white blood cells as well as in the number of bone marrow nucleated cells. This is evident to the protecting effect of the A3RAg against myelotoxic effects of doxorubicin.

EXAMPLE 7

Antibodies Against G-CSF Neutralize the Myeloprotectional Effect of Cl-IB-MECA ICR mice, were divided into six groups as follows:
Group 1: Control—administration of the vehicle only.
Group 2: Control with anti-G-CSF antibodies (5 µg/mouse).
Group 3: Chemotherapy—administration of cyclophosphamide CYP—50 mg/kg body weight).
Group 4: Chemotherapy (50 mg/kg body weight CYP)+ anti-G-CSF antibodies (5 µg/mouse).
Group 5: Chemotherapy (50 mg/kg body weight CYP)+ Cl-IB-MECA (6 µg/kg body weight)+anti-G-CSF antibodies (5 µg/mouse).
Group 6: Chemotherapy (50 mg/kg body weight CYP)+ Cl-IB-MECA (6 µg/kg body weight)+anti-G-CSF antibodies (5 µg/mouse).

Each group consisted of 10 mice and the experiment was repeated twice.

The CYP was injected intraperitoneally in 0.2 ml of PBS which served as the carrier.

Cl-IB-MECA was given orally (in 0.2 ml PBS) at 48 hours and 72 hours following the administration of the cyclophosphamide.

Anti-G-CSF antibodies were intravenously injected (in 0.2 ml PBS) 72 hours following the administration of the chemotherapeutic drugs.

Blood samples were withdrawn 124 hours following chemotherapy. White blood cells (WBC) counts were made in a Coulter counter and differential cell counts were carried on smear preparations stained with May-Grundvald-Giemsa solution.

Figure 13:
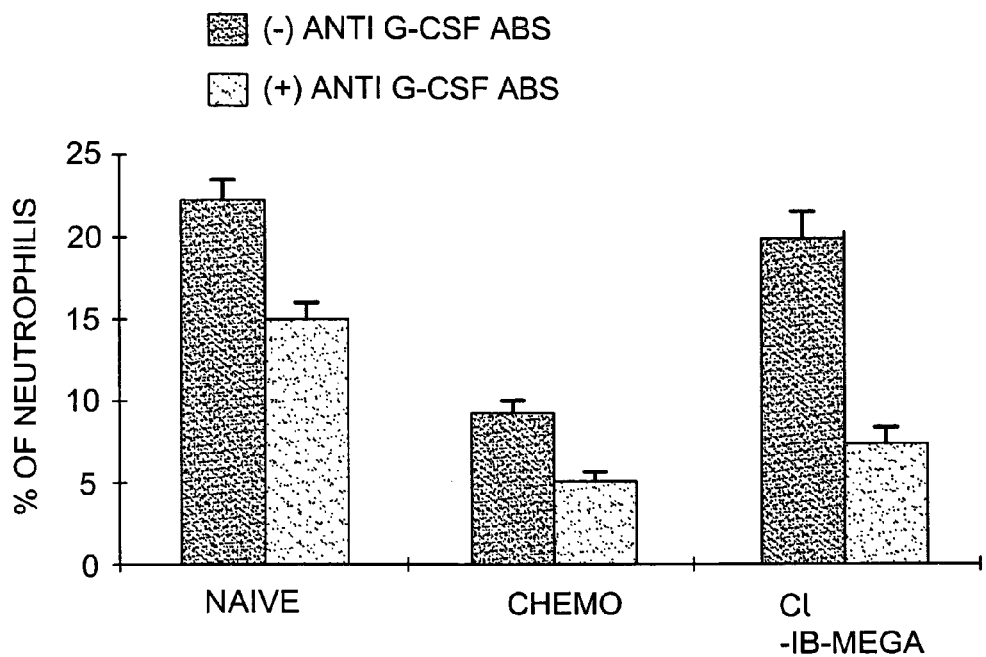
FIG. 13 shows the effect of anti-G-CSF antibodies on the number of white blood cells (WBC) in control mice, mice treated with a chemotherapeutic drug and mice treated with a chemotherapeutic drug and with Cl-IB-MECA, administered orally (6 μg/kg body weight, in 0.2 ml PBS). The number of WBC following injection of anti-G-CSF antibodies is represented by the light-colored columns. All results are presented as percent of control (control=100%).

The results of the WBC count is shown in FIG. 13. As can be seen, mice treated with cyclophosphamide only showed a decline in the number of peripheral blood WBC. In the group that was treated with Cl-IB-MECA, the WBC counts and the percentage of neutrophils were significantly higher in comparison to the chemotherapeutic treated group (results regarding transfer of neutrophils not shown). When anti-G-CSF antibodies were administered to the control or the chemotherapy groups, an expected decline in the number of WBC was observed. Administration of anti-G-CSF antibodies to the mice treated with the combination of the chemotherapeutic drug and Cl-IB-MECA, cancelled the protective effect of Cl-IB-MECA, as can clearly be seen in FIG. 13. These results lead to the conclusion that the protective effect of Cl-IB-MECA on the myeloid system is mediated through the ability of a Cl-IB-MECA to promote the production and secretion of G-CSF.

EXAMPLE 8

Figure 14:
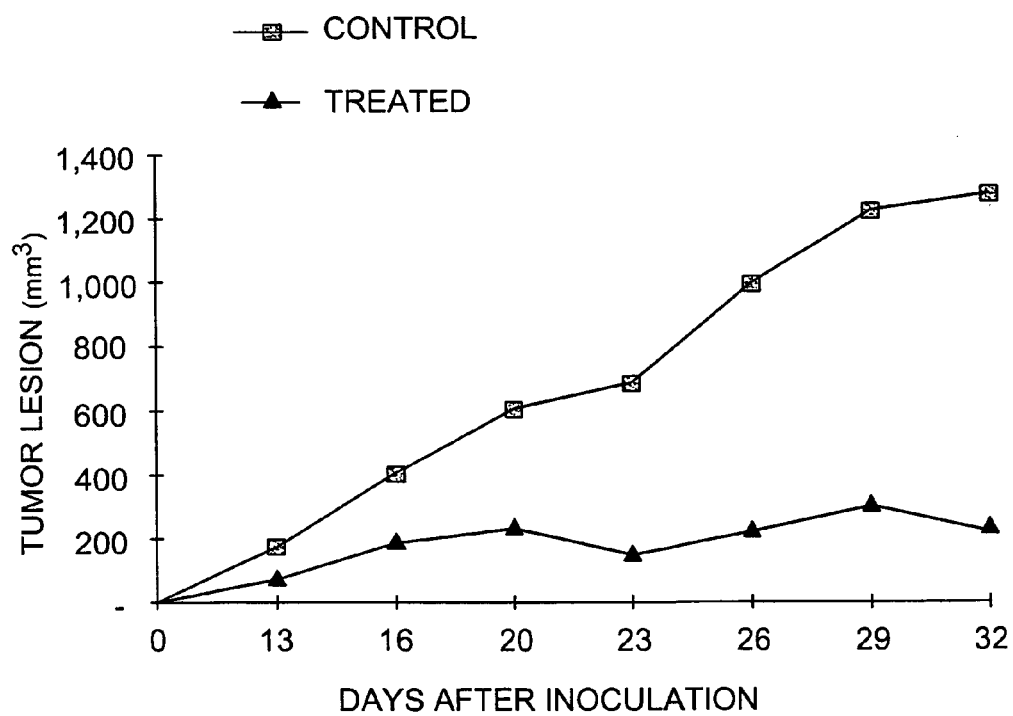
FIG. 14 shows the size of tumor, over time, developed in nude mice following injection of HCT-116 human colon carcinoma cells, in a control group and in a treated group (oral administration of Cl-IB-MECA).

Cl-IB-MECA Inhibits the Development of HCT-116 Human Coon Carcinoma in Nude Mice Tumors were established by subcutaneous injection of $1 \times 10^6$ HCT-116 human colon cancer cells to nude mice (BALB/C origin) (Harlan, Jerusalem, Israel). Mice were treated orally with 6 µg/kg body weight Cl-IB-MECA (in 0.2 ml of PBS) every other day. Mice that were treated with the vehicle only (PBS). Each group consisted of 10 mice. Tumor growth rate was determined by measuring two orthogonal diameters of each tumor twice a week, and the tumor size was estimated according to the following formula: $\pi/6 [D_1 D_2]$. The results are depicted in FIG. 14. As can be seen, in the treated group there is a marked inhibition of tumor growth.

In a separate set of experiments a combined therapy of Cl-IB-MECA and 5-fluorouracyl (5-FU) was tested. $1 \times 10^6$ HCT-116 cells were injected subcutaneously to nude mice. One day later, 5-FU (30 mg/kg body weight, in 0.2 ml PBS) was intraperitoneally injected and subsequently in 4 additional consecutive days. Every other day, the mice were administered orally with 5 µg/kg body weight of Cl-IB- MECA (in 0.2 ml of PBS). Mice that were treated either with the vehicle only (PBS) or with 5-FU served as control. Each group consisted of 10 mice. Tumor growth rate was determined by measuring two orthogonal diameters of each tumor twice a week, and the tumor size was estimated according to the following formula: $\pi/6[D_1 D_2]$.

Figure 15:
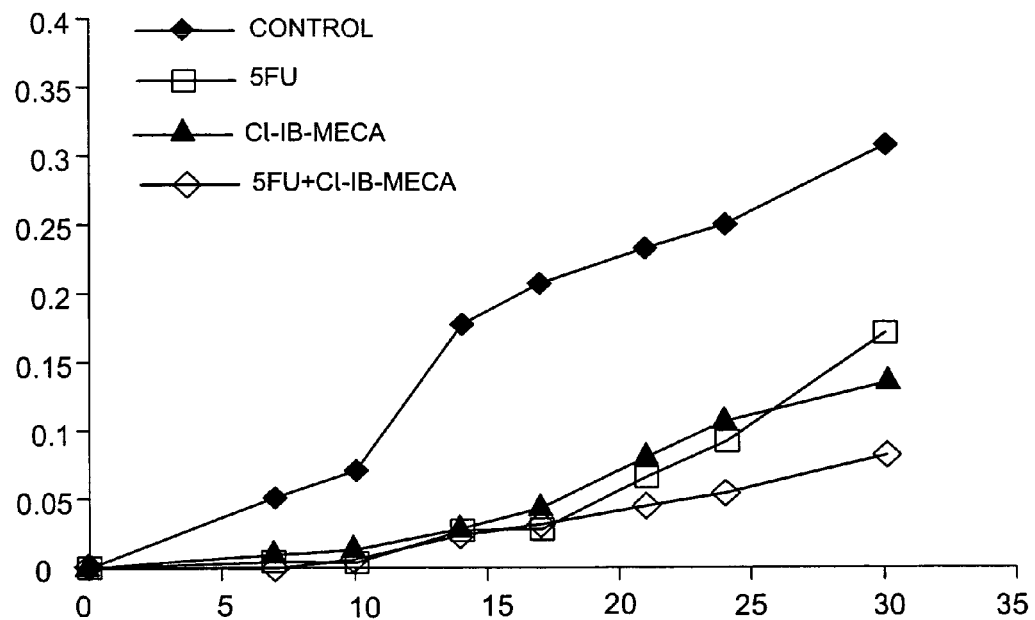
FIG. 15 shows results of experiments similar to that of FIG. 14, where the size of the tumor developed in nude mice following injection of HCT-116 human colon carcinoma cells was measured. Four groups were tested: a control group, a group receiving the chemotherapeutic drug 5-FU, a group administered orally with Cl-IB-MECA and a group receiving a combined treatment of 5-FU and Cl-IB-MECA.
Figure 16:
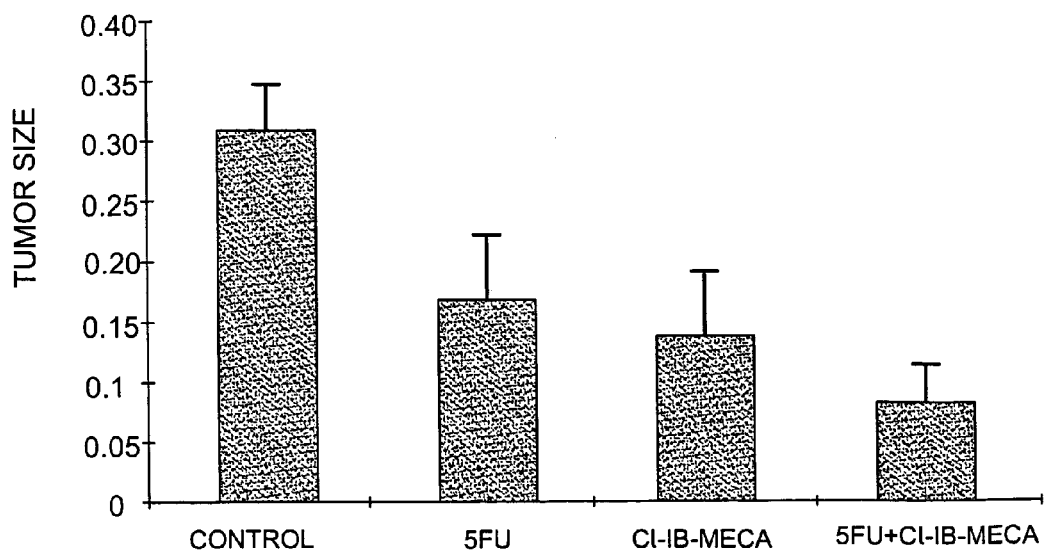
FIG. 16 is a bar graph showing the tumor size at day 30 in the experiment depicted in FIG. 15.

The results are depicted in FIGS. 15 and 16. A marked inhibition of tumor growth was observed in the groups treated with 5-FU, Cl-IB-MECA and the combined therapy of Cl-IB-MECA and 5-FU. After 20 days a clear synergistic effect between Cl-IB-MECA and 5-FU in noting the tumor mass was seen, as depicted particularly in FIG. 16 (the results represented in FIG. 16 are those at day 30).

EXAMPLE 9

Figure 17:
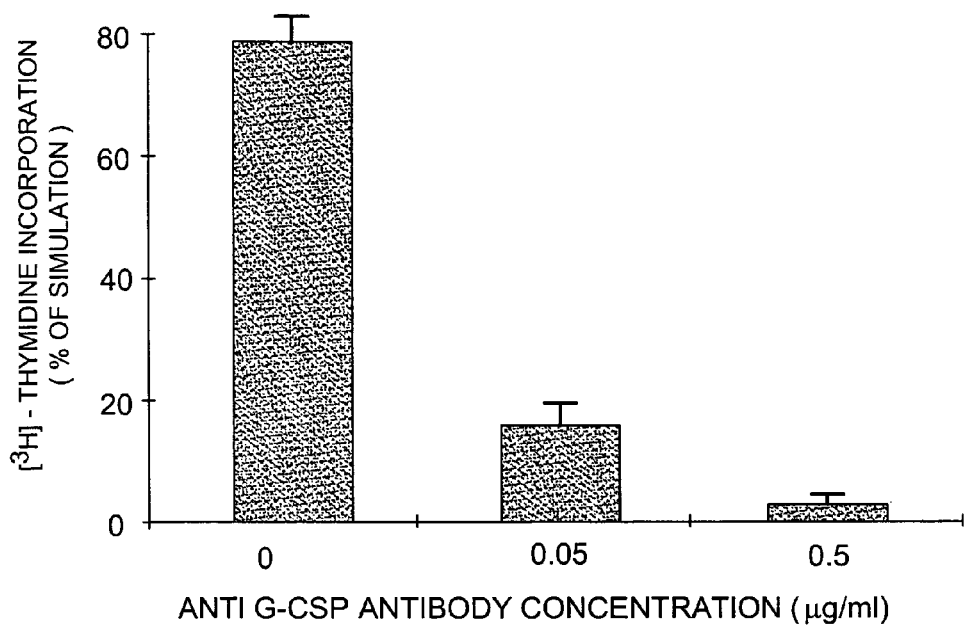
FIG. 17 is a bar graph showing results of an experiment where the Cl-IB-MECA-induced proliferation of bone marrow cells was measured under different concentrations (0.05 µg/ml and 0.5 µg/ml) of anti-G-CSF antibodies (0—no antibodies). The proliferation was determined by [$^3$H]-thymidine incorporation assay.

Cl-IB-MECA Stimulates Bone Marrow Cell Proliferation Through the Induction of G-CSF Production Bone marrow cells ($3\times10^6$ cell/ml) were incubated in wells of 96 microtiter plates. Cl-IB-MECA at a final concentration of 10 nM was added with or without anti-G-CSF antibodies, at a final concentration of 0.05 and 0.5 μg/ml. Cell proliferation was measured by [$^3$H]-thymidine incorporation assay. The results are shown in FIG. 17.

As can be seen, the anti-G-CSF antibodies inhibit the proliferation of the bone marrow cells in a dose-dependent manner. This experiment also shows that the action of Cl-IB-MECA is mediated through the G-CSF pathway (involving G-CSF secretion from the cells).

EXAMPLE 10

Figure 18:
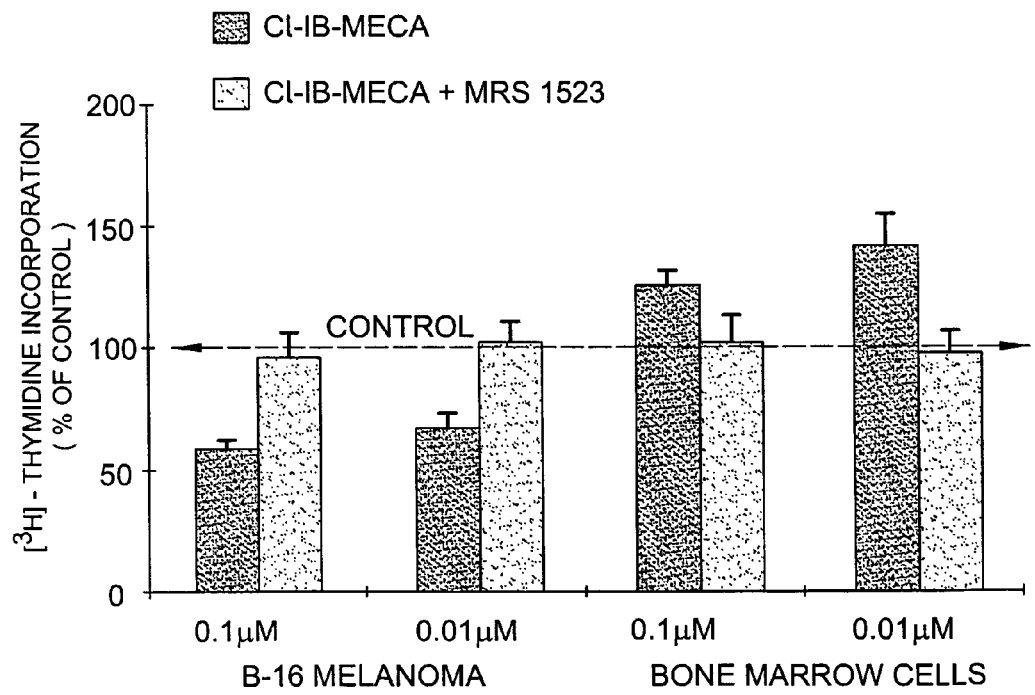
FIG. 18 shows results of an in vitro experiment where proliferation of either B-16 melanoma or bone marrow cells was measured. The proliferation measured was the [$^3$H]-thymidine incorporation assay. The cells were exposed to either 0.01 µM and 0.1 µM Cl-IB-MECA with (white columns) or without (dark columns) the A3RAg, MRS-1523. The results are shown in terms of percent of control (control=100%).

Cl-IB-MECA Inhibits Tumor Cell Growth and Stimulates Bone Marrow Proliferation and Differentiation B-16 melanoma cells ($5\times10^5$ cells/ml) and bone marrow cells ($3\times10^6$ cells/ml) were incubated in wells of 96 microtiter plate. The culture consisted of RPMI medium supplemented with 10% FTS: Cl-IB-MECA, at the concentration of 0.01 μM or 0.1 μM was added, with or without an antagonist of the adenosine A3 receptor, MRS-1523. Cell proliferation was measured by the [$^3$H]-thymidine incorporation assay mentioned before. The results are shown in FIG. 18. As can be seen, in the presence of MRS-1523, the proliferation of both the B-16 melanoma cells and the bone marrow cells was unchanged versus control. Against this, the Cl-IB-MECA exerted an inhibitory effect on proliferation of the B-16 melanoma cells, and a proliferation stimulation effect on the bone marrow cells.

These results demonstrate the dual effect of the A3 adenosine receptor agonists.

EXAMPLE 11

Cl-IB-MECA Acts as a Chemoprotective Agent

Figure 19A:
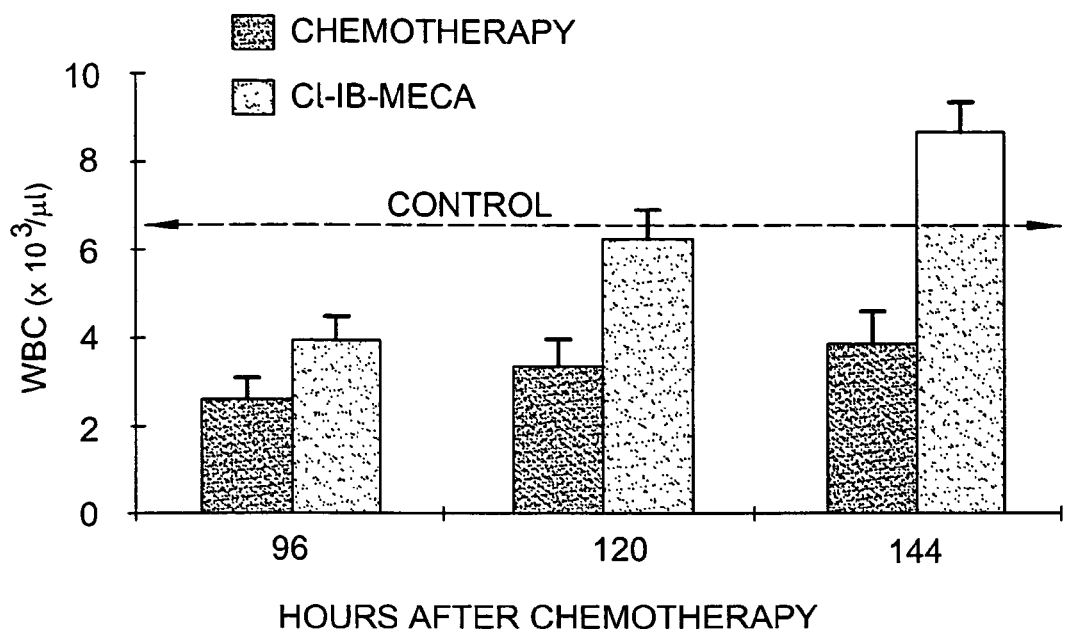
FIGS. 19A and 19B show results of an experiment similar to that shown in FIGS. 10A and 10B, respectively, performed with Cl-IB-MECA.
Figure 19B:
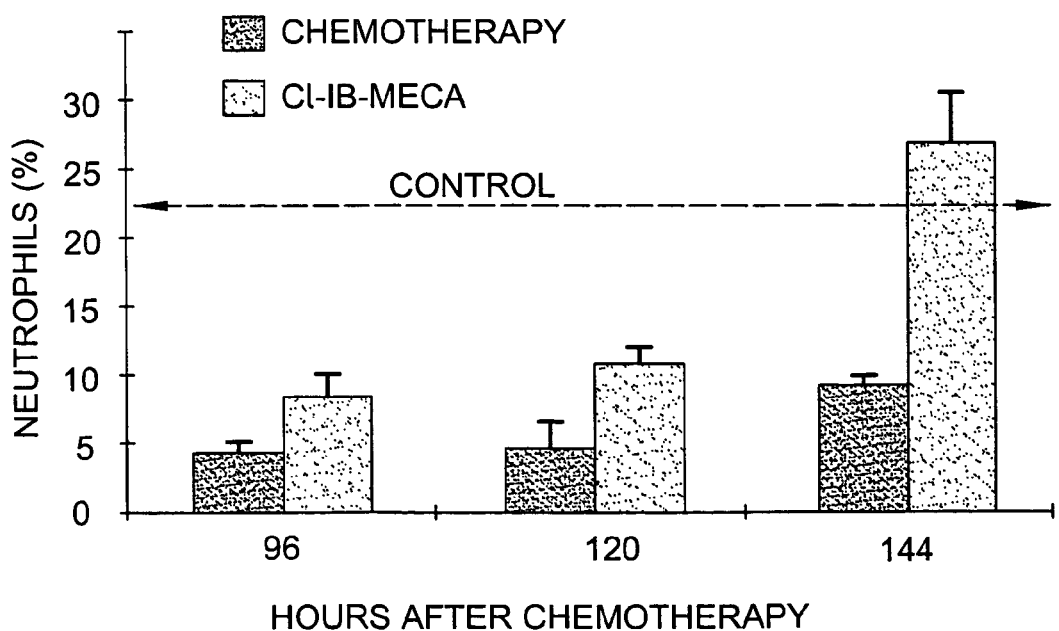

An example similar to that of Example 4, was performed with Cl-IB-MECA and the results are shown in FIGS. 19A and 19B demonstrating the chemoprotective activity of Cl-IB-MECA.

EXAMPLE 12

Effect of IB-MECA and Cl-IB-MECA on the Proliferation of Bone marrow cells

Murine bone marrow cells were cultured as described above. IB-MCA or Cl-IB-MECA were added to the cultures at a concentration of 1 or 10 nM, in the presence or absence of the A3RAn, MRS-1523. The antagonist was added at a concentration of 10 nM. The results are shown in FIG. 20.

Figure 20:
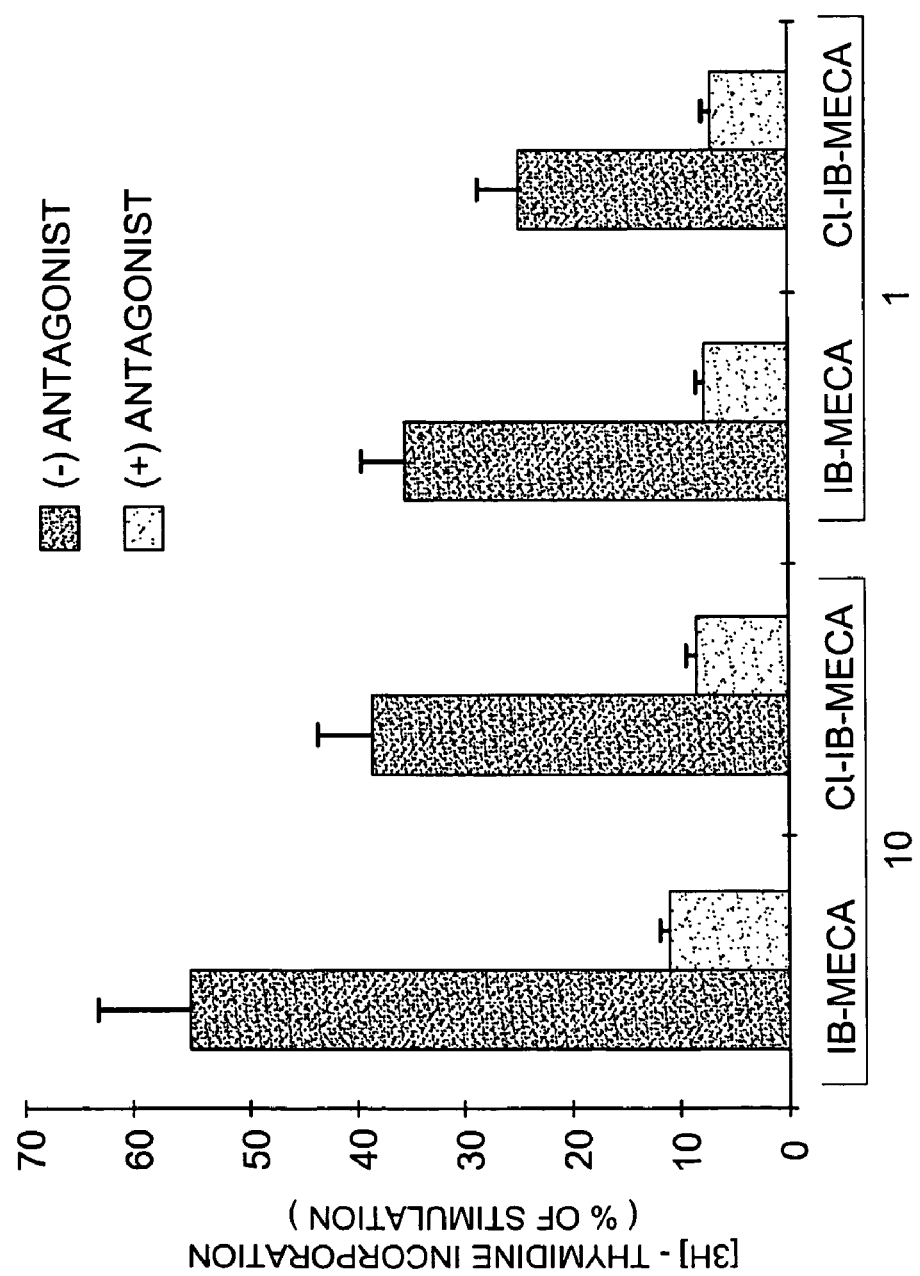
FIG. 20 shows results of an in vitro experiment in which the proliferation of bone marrow cells induced by IB-MECA or Cl-IB-MECA was measured. These two A3RAg were added to the culture of the bone marrow cells at a concentration of either 1 nM or 10 nM, with (gray columns—"(+) antagonists") or without (dark columns—"(−) antagonists"). An A3RAn, MRS-1523, at a concentration of 10 nM. The proliferation was determined by the [$^3$H]-thymidine incorporation assay. The results are given as percent stimulation versus control (untreated bone marrow cells, control=0%).

As can be seen in FIG. 20, the effect of both IB-MECA and Cl-IB-MECA is dose dependent. Furthermore, as can also be seen, this effect is inhibited to a large extent by the A3RAn.

What is claimed is:

1. A method for selectively inhibiting abnormal cell proliferation in a subject in need thereof, comprising administering to the subject an amount of an A3-selective adenosine A3 receptor agonist (A3RAg), in a manner such that it exerts is prime effect through the adenosine A3 receptor, the amount being less than 100 μg/Kg body weight.

2. A method according to claim 1, for inhibiting growth or proliferation of tumor cells.

3. A method according to claim 1, wherein the drug is administered orally.

4. A method according to claim 1, wherein the drug is administered in combination with a chemotherapeutic drug.

5. A method according to claim 1, wherein said active ingredient is an A3-selective A3RAg that is a nucleoside derivative of the following general formula (I):

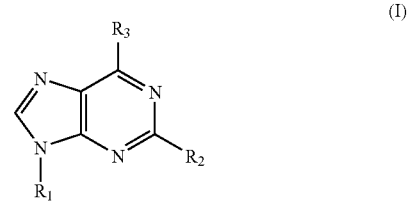

wherein $R_1$ is $C_1$–$C_{10}$ alkyl, $C_1$–$C_{10}$ hydroxyalkyl, $C_1$–$C_{10}$ carboxyalkyl or $C_1$–$C_{10}$ cyanoalkyl or a group of the following general formula (II):

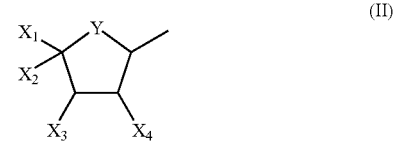

in which:

Y is an oxygen or sulfur atom or $CH_2$;

$X_1$ is H, $C_1$–$C_{10}$ alkyl, $R^a R^b NC(=O)$— or $HOR^c$—, wherein $R^a$ and $R^b$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, $C_1$–$C_{10}$ BOC-aminoalkyl, and $C_3$–$C_{10}$ cycloalkyl or are joined together to form a heterocyclic ring containing two to five carbon atoms, and $R^c$ is selected from the group consisting of $C_1$–$C_{10}$ alkyl, amino, $C_1$–$C_{10}$ haloalkyl, $C_1$–$C_{10}$ aminoalkyl, $C_1$–$C_{10}$ BOC-aminoalkyl, and $C_3$–$C_{10}$ cycloalkyl;

$X_2$ is H, hydroxyl, $C_1$–$C_{10}$ alkylamino, $C_1$–$C_{10}$ alkylamido or $C_1$–$C_{10}$ hydroxyalkyl;

$X_3$ and $X_4$ each independently are hydrogen, hydroxyl, amino, amido, azido, halo, alkyl, alkoxy, carboxy, nitrilo, nitro, trifluoro, aryl, alkaryl, thio, thioester, thioether, —OCOPh, —OC(=S)OPh or both $X_3$ and $X_4$ are oxygen connected to >C=S to form a 5-membered ring, or $X_2$ and $X_3$ form the ring of formula (III):

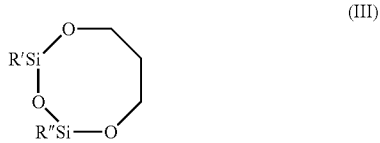

where R' and R" are independently $C_1$–$C_{10}$ alkyl;

$R_2$ is selected from the group consisting of hydrogen, halo, $C_1$–$C_{10}$ alkylether, amino, hydrazido, $C_1$–$C_{10}$ alkylamino, $C_1$–$C_{10}$ alkoxy, $C_1$–$C_{10}$ thioalkoxy, pyridylthio, $C_2$–$C_{10}$ alkenyl; $C_2$–$C_{10}$ alkynyl, thio, and $C_1$–$C_{10}$ alkylthio; and $R_3$ is a —$NR_4R_5$ group with $R_4$ being hydrogen, alkyl, substituted alkyl or aryl-NH—C(Z)—, with Z being O, S or $NR^a$, and, when $R_4$ is hydrogen, $R_5$ being selected from the group consisting of R- and S-1-phenylethyl, benzyl, phenylethyl or anilide groups, each said group being unsubstituted or substituted in one or more positions with a substituent selected from the group consisting of $C_1$–$C_{10}$ alkyl, amino, halo, $C_1$–$C_{10}$ haloalkyl, nitro, hydroxyl, acetamido, $C_1$–$C_{10}$ alkoxy, and sulfonic acid or a salt thereof; or $R_5$ being benzodioxanemethyl, fururyl, L-propylalanylaminobenzyl, β-alanylaminobenzyl, T-BOC-β-alanylaminobenzyl, phenylamino, carbamoyl, phenoxy or $C_1$–$C_{10}$ cycloalkyl; or $R_5$ being a group of the following formula:

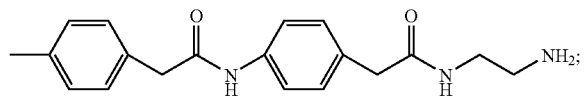

or, when $R_4$ is alkyl, substituted alkyl, or aryl-NH—C(Z)—, then $R_5$ being selected from the group consisting of substituted or unsubstituted heteroaryl-$NR^a$—C(Z), heteroaryl-C(Z)—, alkaryl-$NR^a$—C(Z)—, alkaryl-C(Z)—, aryl-NR—C(Z)— and aryl-C(Z);

or a suitable salt of the compound defined above.

6. A method according to claim 5, wherein said active ingredient is an A3-selective A3RAg that is a nucleoside derivative of the general formula (IV):

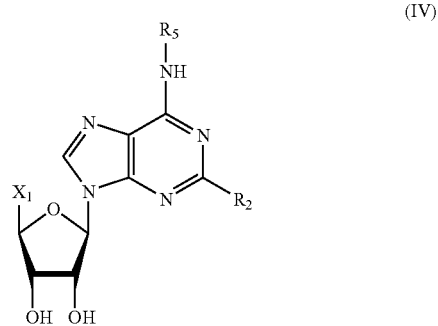

in which $X_1$, $R_2$ and $R_5$ are as defined in claim 5.

7. A method according to claim 6, wherein said active ingredient is an $N^6$-benzyladenosine-5'-uronamide.

8. A method according to claim 7, wherein said active ingredient is selected from the group consisting of $N^6$-2-(4-aminophenyl) ethyladenosine (APNEA), $N^6$-(4-amino-3-iodobenzyl)adenosine-5'-(N-methyluronamide) (AB-MECA) and 1-deoxy-1-{6-[({3-iodophenyl}methyl)amino]-9H-purine-9-yl}-N-methyl-β-D-ribofuranuronamide (IB-MECA) and 2-chloro-$N^6$-(3-iodobenzyl)adenosine-5'-N-methyluronamide (Cl-IB-MECA).

9. A method for treating cancer in a subject in need thereof, which subject is undergoing chemotherapeutic drug treatment, comprising administering to the subject an amount of an A3-selective adenosine A3 receptor agonist (A3RAg), in a manner such that in exerts its prime effect through the adenosine A3 receptor, the amount being effective to both selectively inhibit proliferation of cancer cells and to counter toxic side effects of chemotherapeutic drug treatment of the same subject, wherein said amount is less than 100 μg/Kg body weight.

10. A method according to claim 9, wherein the A3RAg synergizes with said chemotherapeutic drug to yield a stronger anti-tumor effect.

11. A method according to claim 9, wherein the drug is administered orally.

12. A method according to 9, wherein said active ingredient is an A3-selective A3RAg that is a nucleoside derivative of the following general formula (I):

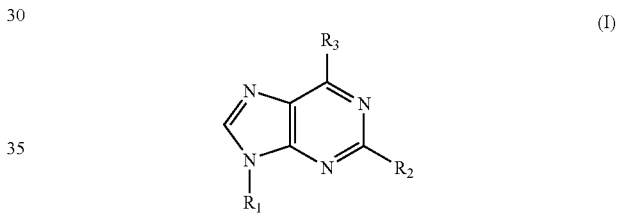

wherein $R_1$ is $C_1$–$C_{10}$ alkyl, $C_1$–$C_{10}$ hydroxyalkyl, $C_1$–$C_{10}$ carboxyalkyl or $C_1$–$C_{10}$ cyanoalkyl or a group of the following general formula (II):

in which:

Y is an oxygen or sulfur atom or $CH_2$;

$X_1$ is H, $C_1$–$C_{10}$ alkyl, $R^a$ $R^b$ NC(=O)— or $HOR^c$—, wherein $R^a$ and $R^b$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, $C_1$–$C_{10}$ BOC-aminoalkyl, and $C_3$–$C_{10}$ cycloalkyl or are joined together to form a heterocyclic ring containing two to five carbon atoms, and $R^c$ is selected from the group consisting of $C_1$–$C_{10}$ alkyl, amino, $C_1$–$C_{10}$ haloalkyl, $C_1$–$C_{10}$ aminoalkyl, $C_1$–$C_{10}$ BOC-aminoalkyl, and $C_3$–$C_{10}$ cycloalkyl;

$X_2$ is H, hydroxyl, $C_1$–$C_{10}$ alkylamino, $C_1$–$C_{10}$ alkylamido or $C_1$–$C_{10}$ hydroxyalkyl;

$X_3$ and $X_4$ each independently are hydrogen, hydroxyl, amino, amido, azido, halo, alkyl, alkoxy, carboxy, nitrilo, nitro, trifluoro, aryl, alkaryl, thio, thioester, thioether, —OCOPh, —OC(=S)OPh or both $X_3$ and X₄ are oxygen connected to >C═S to form a 5-membered ring, or X₂ and X₃ form the ring of formula (III):

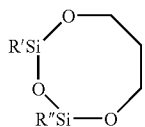

where R' and R" are independently $C_1$–$C_{10}$ alkyl;

R₂ is selected from the group consisting of hydrogen, halo, $C_1$–$C_{10}$ alkylether, amino, hydrazido, $C_1$–$C_{10}$ alkylamino, $C_1$–$C_{10}$ alkoxy, $C_1$–$C_{10}$ thioalkoxy, pyridylthio, $C_2$–$C_{10}$ alkenyl; $C_2$–$C_{10}$ alkynyl, thio, and $C_1$–$C_{10}$ alkylthio; and R₃ is a —NR₄R₅ group with R₄ being hydrogen, alkyl, substituted alkyl or aryl-NH—C(Z)—, with Z being O, S or NR$^a$, and, when R₄ is hydrogen, R₅ being selected from the group consisting of R- and S-1-phenylethyl, benzyl, phenylethyl or anilide groups, each said group being unsubstituted or substituted in one or more positions with a substituent selected from the group consisting of $C_1$–$C_{10}$ alkyl, amino, halo, $C_1$–$C_{10}$ haloalkyl, nitro, hydroxyl, acetamido, $C_1$–$C_{10}$ alkoxy, and sulfonic acid or a salt thereof; or R₅ being benzodioxanemethyl, fururyl, L-propylalanylaminobenzyl, β-alanylaminobenzyl, T-BOC-β-alanylaminobenzyl, phenylamino, carbamoyl, phenoxy or $C_1$–$C_{10}$ cycloalkyl; or R₅ being a group of the following formula:

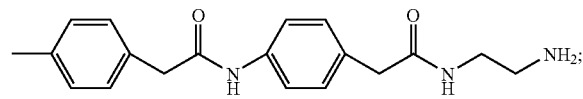

or, when R₄ is alkyl, substituted alkyl, or aryl-NH—C(Z)—, then R₅ being selected from the group consisting of substituted or unsubstituted heteroaryl-NR$^a$—C(Z), heteroaryl-C(Z)—, alkaryl-NR$^a$—C(Z)—, alkaryl-C(Z)—, aryl-NR—C(Z)— and aryl-C(Z);

or a suitable salt of the compound defined above.

13. A method according to claim 12, wherein said active ingredient is an A3-selective A3RAg that is a nucleoside derivative of the general formula (IV):

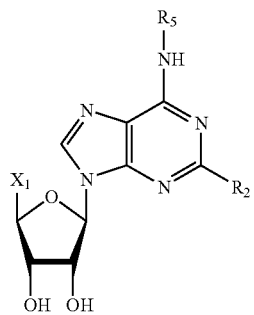

in which X₁, R₂ and R₅ are as defined in claim 12.

14. A method according to claim 13, wherein said active ingredient is an N⁶-benzyladenosine-5'-uronamide.

15. A method according to claim 14, wherein said active ingredient is selected from the group consisting of N⁶-2-(4-aminophenyl)ethyladenosine (APNEA), N⁶-(4-amino-3-iodobenzyl)adenosine-5'-(N-methyluronamide) (AB-MECA) and 1-deoxy-1-{6-[({3-iodophenyl}methyl)amino]-9H-purine-9-yl}N-methyl-β-D-ribofuranuronamide (IB-MECA) and 2- chloro-N⁶(3-iodobenzyl)adenosine-5'-N-methyluronamide (Cl-IB-(MECA).

16. A method for selectively inhibiting abnormal cell proliferation in a subject, comprising administering to the subject an amount of an adenosine A3 receptor agonist (A3RAg) in a manner such that it exerts its prime effect through the A3 adenosine receptor without essentially activating adenosine receptors other than the A3 adenosine receptor, the amount being less than 100 μg/Kg body weight.

17. A method according to claim 16, wherein said abnormal cell proliferation is the growth or proliferation of tumor cells.

18. A method according to claim 16, wherein the drug is administered orally.

19. A method according to claim 16, wherein the drug is administered in combination with a chemotherapeutic drug.

20. A method according to claim 16, wherein the active ingredient is an A3RAg that exerts its prime effect through the A3 adenosine receptor without essentially activating adenosine receptors other then the A3 adenosine receptor, which is a nucleoside derivative of general formula (I):

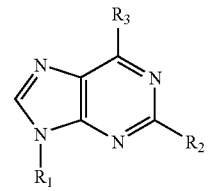

wherein R₁ is $C_1$–$C_{10}$ alkyl, $C_1$–$C_{10}$ hydroxyalkyl, $C_1$–$C_{10}$ carboxyalkyl or $C_1$–$C_{10}$ cyanoalkyl or a group of the following general formula (II):

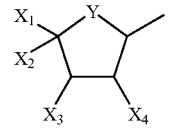

in which:

Y is an oxygen or sulfur atom or CH₂;

X₁ is H, $C_1$–$C_{10}$ alkyl, R$^a$R$^b$NC(═O)— or HOR$^c$—, wherein R$^a$ and R$^b$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, $C_1$–$C_{10}$ BOC-aminoalkyl, and $C_3$–$C_{10}$ cycloalkyl or are joined together to form a heterocyclic ring containing two to five carbon atoms, and R$^c$ is selected from the group consisting of $C_1$–$C_{10}$ alkyl, amino, $C_1$–$C_{10}$ haloalkyl, $C_1$–$C_{10}$ aminoalkyl, $C_1$–$C_{10}$ BOC-aminoalkyl, and $C_3$–$C_{10}$ cycloalkyl;

X₂ is H, hydroxyl, $C_1$–$C_{10}$ alkylamino, $C_1$–$C_{10}$ alkylamido or $C_1$–$C_{10}$ hydroxyalkyl;

X₃ and X₄ each independently are hydrogen, hydroxyl, amino, amido, azido, halo, alkyl, alkoxy, carboxy, nitrilo, nitro, trifluoro, aryl, alkaryl, thio, thioester, thioether, —OCOPh, —OC(═S)OPh or both X₃ and X₄ are oxygen connected to >C═S to form a 5-membered ring, or X₂ and X₃ form the ring of formula (III):

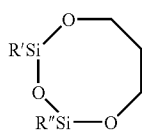

where R' and R" are independently $C_1$–$C_{10}$ alkyl;

$R_2$ is selected from the group consisting of hydrogen, halo, $C_1$–$C_{10}$ alkylether, amino, hydrazido, $C_1$–$C_{10}$ alkylamino, $C_1$–$C_{10}$ alkoxy, $C_1$–$C_{10}$ thioalkoxy, pyridylthio, $C_2$–$C_{10}$ alkenyl, $C_2$–$C_{10}$ alkynyl, thio, and $C_1$–$C_{10}$ alkylthio; and $R_3$ is a —$NR_4R_5$ group with $R_4$ being hydrogen, alkyl, substituted alkyl or aryl-NH—C(Z)—, with Z being O, S or $NR^a$, and, when $R_4$ is hydrogen, $R_5$ being selected from the group consisting of R- and S-1-phenylethyl, benzyl, phenylethyl or anilide groups, each said group being unsubstituted or substituted in one or more positions with a substituent selected from the group consisting of $C_1$–$C_{10}$ alkyl, amino, halo, $C_1$–$C_{10}$ haloalkyl, nitro, hydroxyl, acetamido, $C_1$–$C_{10}$ alkoxy, and sulfonic acid or a salt thereof; or $R_5$ being benzodioxanemethyl, fururyl, L-propylalanyl-aminobenzyl, β-alanylamino-benzyl, T-BOC-β-alanylaminobenzyl, phenylamino, carbamoyl, phenoxy or $C_1$–$C_{10}$ cycloalkyl; or $R_5$ being a group of the following formula:

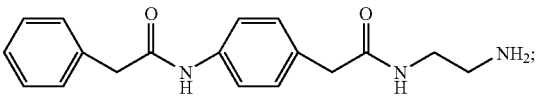

or, when $R_4$ is alkyl, substituted alkyl, or aryl-NH—C(Z)—, then $R_5$ is selected from the group consisting of substituted or unsubstituted heteroaryl-$NR^a$—C(Z)—, heteroaryl-C(Z)—, alkaryl-$NR^a$—C(Z)—, alkaryl-C(Z)—, aryl-NR—C(Z)— and aryl-C(Z)—;

or a suitable salt of said nucleotide derivative.

21. A method according to claim 20, wherein said active ingredient is an A3RAg that exerts its prime effect through the A3 adenosine receptor without essentially activating adenosine receptors other then the A3 adenosine receptor, which is a nucleoside derivative of the general formula (IV):

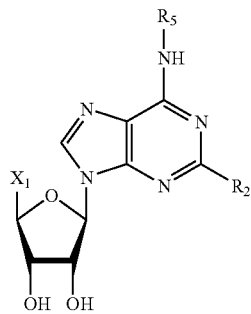

in which $X_1$, $R_2$ and $R_4$ are as defined in claim 20.

22. A method according to claim 21, wherein said active ingredient is an $N^6$-benzyladenosine-5'-uronamide.

23. A method according to claim 22, wherein said active ingredient is selected from the group consisting of $N^6$-2-(4-aminophenyl)ethyladenosine (APNEA), $N^6$-(4-amino-3-iodobenzyl) adenosine-5'-(N-methyluronamide) (AB-MECA) and 1-deoxy-1-{6-[({3-iodophenyl}methyl)amino]-9H-purine-9-yl}-N-methyl-β-D-ribofuranuron-amide (IB-MECA) and 2-chloro-$N^6$-(3-iodobenzyl)-adenosine-5'-N-methlyuronamide (Cl-IB-MECA).

24. A method according to claim 16, wherein the amount is less than 50 μg/Kg body weight.

25. A method according to claim 20, wherein said active ingredient is selected from the group consisting of:

$N^6$-(3-iodobenzyl)-9-methyladenine;
$N^6$-(3-iodobenzyl)-9-hydroxyethyladenine;
R—$N^6$-(3-iodobenzyl)-9-(2,3-dihydroxypropyl)adenine;
S—$N^6$-(3-iodobenzyl)-9-(2,3-dihydroxypropyl)adenine;
$N^6$-(3-iodobenzyladenin-9-yl)acetic acid;
$N^6$-(3-iodobenzyl)-9-(3-cyanopropyl)adenine;
2-chloro-$N^6$-(3-iodobenzyl)-9-methyladenine;
2-amino-$N^6$-(3-iodobenzyl)-9-methyladenine;
2-hydrazido-$N^6$-(3-iodobenzyl)-9-methyladenine;
$N^6$-(3-iodobenzyl)-2-methylamino-9-methyladenine;
2-dimethylamino-$N^6$-(3-iodobenzyl)-9-methyladenine;
$N^6$-(3-iodobenzyl)-9-methyl-2-propylaminoadenine;
2-hexylamino-$N^6$-(3-iodobenzyl)-9-methyladenine;
$N^6$-(3-iodobenzyl)-2-methoxy-9-methyladenine;
$N^6$-(3-iodobenzyl)-9-methyl-2-methylthioadenine;
$N^6$-(3-iodobenzyl)-9-methyl-2-(4-pyridylthio)adenine;
(1S,2R,3S,4R)-4-(6-amino-2-phenylethylamino-9H-purin-9-yl)cyclopentane-1,2,3-triol;
(1S,2R,3S,4R)-4-(6-amino-2-chloro-9H-purin-9-yl) cyclopentane-1,2,3-triol;
(±)-9-[2α,3α-dihydroxy-4β-(N-methylcarbamoyl)cyclopent-1β-yl)]-$N^6$-(3-iodobenzyl)-adenine;
2-chloro-9-(2'-amino-2',3'-dideoxy-β-D-5'-methyl-arabino-furonamido)-$N^6$-(3-iodobenzyl)adenine;
2-chloro-9-(2',3'-dideoxy-2'-fluoro-β-D-5'-methyl-arabino-furonamido)-$N^6$-(3-iodobenzyl)adenine;
9-(2-acetyl-3-deoxy-β-D-5-methyl-ribofuronamido)-2-chloro-$N^6$(3-iodobenzyl)adenine;
2-chloro-9-(3-deoxy-2-methanesulfonyl-β-D-5-methyl-ribofuronamido)-$N^6$-(3-iodobenzyl)adenine;
2-chloro-9-(3-deoxy-β-D-5-methyl-ribofuronamido)-$N^6$-(3-iodobenzyl)adenine;
2-chloro-9-(3,5-1,1,3,3-tetraisopropyldisiloxyl-β-D-5-ribofuranosyl) —$N^6$—(3-iodobenzyl) adenine;
2-chloro-9-(2',3'-O-thiocarbonyl-β-D-5-methyl-ribofuronamido)-$N^6$-(3-iodobenzyl)adenine;
9-(2-phenoxythiocarbonyl-3-deoxy-β-D-5-methyl-ribofuronamido)-2-chloro-$N^6$-(3-iodobenzyl)adenine;
1-(6-benzylamino-9H-purin-9-yl)-1-deoxy-N,4-dimethyl-β-D-ribofuranosiduronamide;
2-chloro-9-(2,3-dideoxy-β-D-5-methyl-ribofuronamido) —$N^6$-benzyladenine;
2-chloro-9-(2'-azido-2',3'-dideoxy-β-D-5'-methyl-arabino-furonamido)-$N^6$-benzyladenine;
2-chloro-9-(β-D-erythrofuranoside)-$N^6$-(3-iodobenzyl) adenine;
$N^6$-(benzodioxanemethyl)adenosine;
1-(6-furfurylamino-9H-purin-9-yl)-1-deoxy-N-methyl-β-D-ribofuranosiduronamide;
$N^6$-[3-(L-prolylamino)benzyl]adenosine-5'-N-methyluronamide;
$N^6$-[3-(β-alanylamino)benzyl]adenosine-5'-N-methyluronamide;
$N^6$-[3-(N—T-Boc-β-alanylamino)benzyl]adenosine-5'-N-methyluronamide 6-(N'-phenylhydrazinyl)purine-9-β-ribofuranoside-5'-N-methyluronamide;
6-(O-phenylhydroxylamino)purine-9-β-ribofuranoside-5'-N-methyluronamide;
9-(β-D-2',3'-dideoxyerythrofuranosyl)-N$^6$-[(3-β-alanylamino)benzyl]adenosine;
9-(β-D-erythrofuranoside)-2-methylamino-N$^6$-(3-iodobenzyl)adenine;
2-chloro-N-(3-iodobenzyl)-9-(2-tetrahydrofuryl)-9H-purin-6-amine;
2-chloro-(2'-deoxy-6'-thio-L-arabinosyl)adenine;
2-chloro-(6'-thio-L-arabinosyl)adenine;
N$^6$-(4-biphenyl-carbonylamino)-adenosine-5'-N-ethyluronamide;
N$^6$-(2,4-dichlorobenzyl-carbonylamino)-adenosine-5'-N-ethyluronamide;
N$^6$-(4-methoxyphenyl-carbonylamino)-adenosine-5'-N-ethyluronamide;
N$^6$-(4-chlorophenyl-carbonylamino)-adenosine-5'-N-ethyluronamide;
N$^6$-(phenyl-carbonylamino)-adenosine-5'-N-ethyluronamide;
N$^6$-(benzylcarbamoylamino)-adenosine-5'-N-ethyluronamide;
N$^6$-(4-sulfonamido-phenylcarbamoyl)-adenosine-5'-N-ethyluronamide;
N$^6$-(4-acetyl-phenylcarbamoyl)-adenosine-5'-N-ethyluronamide;
N$^6$-((R)-α-phenylethylcarbamoyl)-adenosine-5'-N-ethyluronamide;
N$^6$-((S)-α-phenylethylcarbamoyl)-adenosine-5'-N-ethyluronamide;
N$^6$-(5-methyl-isoxazol-3-yl-carbamoyl)-adenosine-5'-N-ethyluronamide;
N$^6$-(1,3,4-thiadiazol-2-yl-carbamoyl)-adenosine-5'-N-ethyluronamide;
N$^6$-(4-n-propoxy-phenylcarbamoyl)-adenosine-5'-N-ethyluronamide;
N$^6$-bis-(4-nitrophenylcarbamoyl)-adenosine-5'-N-ethyluronamide; and
N$^6$-bis-(5-chloro-pyridin-2-yl-carbamoyl)-adenosine-5'-N-ethyluronamide.

26. A method according to claim 21, wherein said active ingredient is an A3 selective A3RAg that is selected from the group consisting of those of formula (IV) in which:
X$_1$ is R$^a$R$^b$NC(=O), wherein R$^a$ and R$^b$ may be the same or different and are selected from the group consisting of hydrogen, C$_1$–C$_{10}$ alkyl, amino, C$_1$–C$_{10}$ haloalkyl, C$_1$–C$_{10}$ aminoalkyl, and C$_3$–C$_{10}$ cycloalkyl, R$_2$ is selected from the group consisting of hydrogen, halo, C$_1$–C$_{10}$ alkyoxy, amino, C$_2$–C$_{10}$ alkenyl, and C$_2$–C$_{10}$ alkynyl, and R$_5$ is selected from the group consisting of R- and S-1-phenylethyl, an unsubstituted benzyl group, and a benzyl group substituted in one or more positions with a substituent selected from the group consisting of C$_1$–C$_{10}$ alkyl, amino, halo, C$_1$–C$_{10}$ haloalkyl, nitro, hydroxy, acetamido, C$_1$–C$_{10}$ alkoxy, and sulfo.

27. A method according to claim 26, wherein said active ingredient is an A3 selective A3RAg that is selected from the group consisting of those of formula (IV) in which:
R$^a$ and R$^b$ are the same or different and are selected from the group consisting of hydrogen and C$_1$–C$_{10}$ alkyl, and R$_2$ is hydrogen or halo;
R$^a$ is hydrogen, R$_2$ is hydrogen and R$_5$ is unsubstituted benzyl;
R$^b$ is C$_1$–C$_{10}$ alkyl or C$_3$–C$_{10}$ cycloalkyl and R$_5$ in R- or S-1-phenylethyl or a benzyl substituted in one or more positions with a substituent selected from the group consisting of halo, amino, acetamido, C$_1$–C$_{10}$ haloalkyl and sulfo, wherein the sulfo derivative is a salt;
R$_2$ is a C$_2$–C$_{10}$ alkyne of the formula R$^d$—C≡C— where R$^d$ is a C$_1$–C$_8$ alkyl; or
R$_2$ is a halo, C$_1$–C$_{10}$ alkylamino, or C$_1$–C$_{10}$ alkylthio, R$^a$ is hydrogen, R$^b$ is C$_1$–C$_{10}$ alkyl and R$_5$ is a substituted benzyl.

28. A method according to claim 20, wherein the active ingredient is an A3 selective A3RAg that is in the form of a triethylammonium salt.

29. A method according to claim 5, wherein said active ingredient is selected from the group consisting of:
N$^6$-(3-iodobenzyl)-9-methyladenine;
N$^6$-(3-iodobenzyl)-9-hydroxyethyladenine;
R—N$^6$-(3-iodobenzyl)-9-(2,3-dihydroxypropyl)adenine;
S—N$^6$-(3-iodobenzyl)-9-(2,3-dihydroxypropyl)adenine;
N$^6$-(3-iodobenzyladenin-9-yl)acetic acid;
N$^6$-(3-iodobenzyl)-9-(3-cyanopropyl)adenine;
2-chloro-N$^6$-(3-iodobenzyl)-9-methyladenine;
2-amino-N$^6$-(3-iodobenzyl)-9-methyladenine;
2-hydrazido-N$^6$-(3-iodobenzyl)-9-methyladenine;
N$^6$-(3-iodobenzyl)-2-methylamino-9-methyladenine;
2-dimethylamino-N$^6$-(3-iodobenzyl)-9-methyladenine;
N$^6$-(3-iodobenzyl)-9-methyl-2-propylaminoadenine;
2-hexylamino-N$^6$-(3-iodobenzyl)-9-methyladenine;
N$^6$-(3-iodobenzyl)-2-methoxy-9-methyladenine;
N$^6$-(3-iodobenzyl)-9-methyl-2-methylthioadenine;
N$^6$-(3-iodobenzyl)-9-methyl-2-(4-pyridylthio)adenine;
(1S,2R,3S,4R)-4-(6-amino-2-phenylethylamino-9H-purin-9-yl)cyclopentane-1,2,3-triol;
(1S,2R,3S,4R)-4-(6-amino-2-chloro-9H-purin-9-yl)cyclopentane-1,2,3-triol;
(±)-9-[2α,3α-dihydroxy-4β-(N-methylcarbamoyl)cyclopent-1β-yl)]-N$^6$-(3-iodobenzyl)-adenine;
2-chloro-9-(2'-amino-2',3'-dideoxy-β-D-5'-methyl-arabino-furonamido)-N$^6$-(3-iodobenzyl)adenine;
2-chloro-9-(2',3'-dideoxy-2'-fluoro-β-D-5'-methyl-arabino-furonamido)-N$^6$-(3-iodobenzyl)adenine;
9-(2-acetyl-3-deoxy-β-D-5-methyl-ribofuronamido)-2-chloro-N$^6$(3-iodobenzyl)adenine;
2-chloro-9-(3-deoxy-2-methanesulfonyl-β-D-5-methyl-ribofuronamido)-N$^6$-(3-iodobenzyl)adenine;
2-chloro-9-(3-deoxy-β-D-5-methyl-ribofuronamido)-N$^6$-(3-iodobenzyl)adenine;
2-chloro-9-(3,5-1,1,3,3-tetraisopropyldisiloxyl-β-D-5-ribofuranosyl)-N$^6$-(3-iodobenzyl)adenine;
2-chloro-9-(2',3'-O-thiocarbonyl-β-D-5-methyl-ribofuronamido)-N$^6$-(3-iodobenzyl)adenine;
9-(2-phenoxythiocarbonyl-3-deoxy-β-D-5-methyl-ribofuronamido)-2-chloro-N$^6$-(3-iodobenzyl)adenine;
1-(6-benzylamino-9H-purin-9-yl)-1-deoxy-N,4-dimethyl-β-D-ribofuranosiduronamide;
2-chloro-9-(2,3-dideoxy-β-D-5-methyl-ribofuronamido)-N$^6$-benzyladenine;
2-chloro-9-(2'-azido-2',3'-dideoxy-β-D-5'-methyl-arabino-furonamido)-N$^6$-benzyladenine;
2-chloro-9-(β-D-erythrofuranoside)-N$^6$-(3-iodobenzyl)adenine;
N$^6$-(benzodioxanemethyl)adenosine;
1-(6-furfurylamino-9H-purin-9-yl)-1-deoxy-N-methyl-β-D-ribofuranosiduronamide;
N$^6$-[3-(L-prolylamino)benzyl]adenosine-5'-N-methyluronamide;
N$^6$-[3-(β-alanylamino)benzyl]adenosine-5'-N-methyluronamide;

N⁶-[3-(N—T-Boc-β-alanylamino)benzyl]adenosine-5'-N-methyluronamide
6-(N'-phenylhydrazinyl)purine-9-β-ribofuranoside-5'-N-methyluronamide;
6-(O-phenylhydroxylamino)purine-9-β-ribofuranoside-5'-N-methyluronamide;
9-(β-D-2',3'-dideoxyerythrofuranosyl)-N⁶-[(3-β-alanylamino)benzyl]adenosine;
9-(β-D-erythrofuranoside)-2-methylamino-N⁶-(3-iodobenzyl)adenine;
2-chloro-N-(3-iodobenzyl)-9-(2-tetrahydrofuryl)-9H-purin-6-amine;
2-chloro-(2'-deoxy-6'-thio-L-arabinosyl)adenine;
2-chloro-(6'-thio-L-arabinosyl)adenine;
N⁶-(4-biphenyl-carbonylamino)-adenosine-5'-N-ethyluronamide;
N⁶-(2,4-dichlorobenzyl-carbonylamino)-adenosine-5'-N-ethyluronamide;
N⁶-(4-methoxyphenyl-carbonylamino)-adenosine-5'-N-ethyluronamide;
N⁶-(4-chlorophenyl-carbonylamino)-adenosine-5'-N-ethyluronamide;
N⁶-(phenyl-carbonylamino)-adenosine-5'-N-ethyluronamide;
N⁶-(benzylcarbamoylamino)-adenosine-5'-N-ethyluronamide;
N⁶-(4-sulfonamido-phenylcarbamoyl)-adenosine-5'-N-ethyluronamide;
N⁶-(4-acetyl-phenylcarbamoyl)-adenosine-5'-N-ethyluronamide;
N⁶-((R)-α-phenylethylcarbamoyl)-adenosine-5'-N-ethyluronamide;
N⁶-((S)-α-phenylethylcarbamoyl)-adenosine-5'-N-ethyluronamide;
N⁶-(5-methyl-isoxazol-3-yl-carbamoyl)-adenosine-5'-N-ethyluronamide;
N⁶-(1,3,4-thiadiazol-2-yl-carbamoyl)-adenosine-5'-N-ethyluronamide;
N⁶-(4-n-propoxy-phenylcarbamoyl)-adenosine-5'-N-ethyluronamide;
N⁶-bis-(4-nitrophenylcarbamoyl)-adenosine-5'-N-ethyluronamide; and
N⁶-bis-(5-chloro-pyridin-2-yl-carbamoyl)-adenosine-5'-N-ethyluronamide.

30. A method according to claim 12, wherein said active ingredient is selected from the group consisting of:
N⁶-(3-iodobenzyl)-9-methyladenine;
N⁶-(3-iodobenzyl)-9-hydroxyethyladenine;
R—N⁶-(3-iodobenzyl)-9-(2,3-dihydroxypropyl)adenine;
S—N⁶-(3-iodobenzyl)-9-(2,3-dihydroxypropyl)adenine;
N⁶-(3-iodobenzyladenin-9-yl)acetic acid;
N⁶-(3-iodobenzyl)-9-(3-cyanopropyl)adenine;
2-chloro-N⁶-(3-iodobenzyl)-9-methyladenine;
2-amino-N⁶-(3-iodobenzyl)-9-methyladenine;
2-hydrazido-N⁶-(3-iodobenzyl)-9-methyladenine;
N⁶-(3-iodobenzyl)-2-methylamino-9-methyladenine;
2-dimethylamino-N⁶-(3-iodobenzyl)-9-methyladenine;
N⁶-(3-iodobenzyl)-9-methyl-2-propylaminoadenine;
2-hexylamino-N⁶-(3-iodobenzyl)-9-methyladenine;
N⁶-(3-iodobenzyl)-2-methoxy-9-methyladenine;
N⁶-(3-iodobenzyl)-9-methyl-2-methylthioadenine;
N⁶-(3-iodobenzyl)-9-methyl-2-(4-pyridylthio)adenine;
(1S,2R,3S,4R)-4-(6-amino-2-phenylethylamino-9H-purin-9-yl)cyclopentane-1,2,3-triol;
(1S,2R,3S,4R)-4-(6-amino-2-chloro-9H-purin-9-yl)cyclopentane-1,2,3-triol;
(±)-9-[2α,3α-dihydroxy-4β-(N-methylcarbamoyl)cyclopent-1β-yl)]-N⁶-(3- iodobenzyl)-adenine;
2-chloro-9-(2'-amino-2',3'-dideoxy-β-D-5'-methyl-arabino-furonamido)-N⁶-(3-iodobenzyl)adenine;
2-chloro-9-(2',3'-dideoxy-2'-fluoro-β-D-5'-methyl-arabino-furonamido)-N⁶-(3-iodobenzyl)adenine;
9-(2-acetyl-3-deoxy-β-D-5-methyl-ribofuronamido)-2-chloro-N⁶(3-iodobenzyl)adenine;
2-chloro-9-(3-deoxy-2-methanesulfonyl-β-D-5-methyl-ribofuronamido)-N⁶-(3-iodobenzyl) adenine;
2-chloro-9-(3-deoxy-β-D-5-methyl-ribofuronamido)-N⁶-(3-iodobenzyl)adenine;
2-chloro-9-(3,5-1,1,3,3-tetraisopropyldisiloxyl-β-D-5-ribofuranosyl)-N⁶-(3-iodobenzyl)adenine;
2-chloro-9-(2',3'-O-thiocarbonyl-β-D-5-methyl-ribofuronamido)-N⁶-(3-iodobenzyl)adenine;
9-(2-phenoxythiocarbonyl-3-deoxy-β-D-5-methyl-ribofuronamido)-2-chloro-N⁶-(3- iodobenzyl)adenine;
1-(6-benzylamino-9H-purin-9-yl)-1-deoxy-N,4-dimethyl-β-D-ribofuranosiduronamide;
2-chloro-9-(2,3-dideoxy-β-D-5-methyl-ribofuronamido)-N⁶-benzyladenine;
2-chloro-9-(2'-azido-2',3'-dideoxy-β-D-5'-methyl-arabino-furonamido)-N⁶-benzyladenine;
2-chloro-9-(β-D-erythrofuranoside)-N⁶-(3-iodobenzyl) adenine;
N⁶-(benzodioxanemethyl)adenosine;
1-(6-furfurylamino-9H-purin-9-yl)-1-deoxy-N-methyl-β-D-ribofuranosiduronamide;
N⁶-[3-(L-prolylamino)benzyl]adenosine-5'-N-methyluronamide;
N⁶-[3-(β-alanylamino)benzyl]adenosine-5'-N-methyluronamide;
N⁶-[3-(N—T-Boc-β-alanylamino)benzyl]adenosine-5'-N-methyluronamide
6-(N'-phenylhydrazinyl)purine-9-β-ribofuranoside-5'-N-methyluronamide;
6-(O-phenylhydroxylamino)purine-9-β-ribofuranoside-5'-N-methyluronamide;
9-(β-D-2',3'-dideoxyerythrofuranosyl)-N⁶-[(3-β-alanylamino)benzyl]adenosine;
9-(β-D-erythrofuranoside)-2-methylamino-N⁶-(3-iodobenzyl)adenine;
2-chloro-N-(3-iodobenzyl)-9-(2-tetrahydrofuryl)-9H-purin-6-amine;
2-chloro-(2'-deoxy-6'-thio-L-arabinosyl)adenine;
2-chloro-(6'-thio-L-arabinosyl)adenine;
N⁶-(4-biphenyl-carbonylamino)-adenosine-5'-N-ethyluronamide;
N⁶-(2,4-dichlorobenzyl-carbonylamino)-adenosine-5'-N-ethyluronamide;
N⁶-(4-methoxyphenyl-carbonylamino)-adenosine-5'-N-ethyluronamide;
N⁶-(4-chlorophenyl-carbonylamino)-adenosine-5'-N-ethyluronamide;
N⁶-(phenyl-carbonylamino)-adenosine-5'-N-ethyluronamide;
N⁶-(benzylcarbamoylamino)-adenosine-5'-N-ethyluronamide;
N⁶-(4-sulfonamido-phenylcarbamoyl)-adenosine-5'-N-ethyluronamide;
N⁶-(4-acetyl-phenylcarbamoyl)-adenosine-5'-N-ethyluronamide;
N⁶-((R)-α-phenylethylcarbamoyl)-adenosine-5'-N-ethyluronamide;
N⁶-((S)-α-phenylethylcarbamoyl)-adenosine-5'-N-ethyluronamide;

N$^6$-(5-methyl-isoxazol-3-yl-carbamoyl)-adenosine-5'-N-ethyluronamide;

N$^6$-(1,3,4-thiadiazol-2-yl-carbamoyl)-adenosine-5'-N-ethyluronamide;

N$^6$-(4-n-propoxy-phenylcarbamoyl)-adenosine-5'-N-ethyluronamide;

N$^6$-bis-(4-nitrophenylcarbamoyl)-adenosine-5'-N-ethyluronamide; and

N$^6$-bis-(5-chloro-pyridin-2-yl-carbamoyl)-adenosine-5'-N-ethyluronamide.

31. A method according to claim 5, wherein the active ingredient is an A3 selective A3RAg that is in the form of a triethylammonium salt.

32. A method according to claim 12, wherein the active ingredient is an A3 selective A3RAg that is in the form of a triethylammonium salt.

33. A method according to claim 6, wherein said active ingredient is an A3 selective A3RAg that is selected from the group consisting of those of formula (IV) in which:

$X_1$ is $R^aR^bNC(=O)$, wherein $R^a$ and $R^b$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, and $C_3$–$C_{10}$ cycloalkyl, $R_2$ is selected from the group consisting of hydrogen, halo, $C_1$–$C_{10}$ alkyoxy, amino, $C_2$–$C_{10}$ alkenyl, and $C_2$–$C_{10}$ alkynyl, and $R_4$ is selected from the group consisting of R- and S-1-phenylethyl, an unsubstituted benzyl group, and a benzyl group substituted in one or more positions with a substituent selected from the group consisting of $C_1$–$C_{10}$ alkyl, amino, halo, $C_1$–$C_{10}$ haloalkyl, nitro, hydroxy, acetamido, $C_1$–$C_{10}$ alkoxy, and sulfo.

34. A method according to claim 33, wherein said active ingredient is an A3 selective A3RAg that is selected from the group consisting of those of formula (IV) in which:

$R^a$ and $R^b$ are the same or different and are selected from the group consisting of hydrogen and $C_1$–$C_{10}$ alkyl, and $R_2$ is hydrogen or halo;

$R^a$ is hydrogen, $R_2$ is hydrogen and $R_5$ is unsubstituted benzyl;

$R^b$ is $C_1$–$C_{10}$ alkyl or $C_3$–$C_{10}$ cycloalkyl and $R_5$ in R- or S-1-phenylethyl or a benzyl substituted in one or more positions with a substituent selected from the group consisting of halo, amino, acetamido, $C_1$–$C_{10}$ haloalkyl and sulfo, wherein the sulfo derivative is a salt;

$R_2$ is a $C_2$–$C_{10}$ alkyne of the formula $R^d$—C≡C— where $R^d$ is a $C_1$–$C_8$ alkyl; or $R_2$ is a halo, $C_1$–$C_{10}$ alkylamino, or $C_1$–$C_{10}$ alkylthio, $R^a$ is hydrogen, $R^b$ is $C_1$–$C_{10}$ alkyl and $R_5$ is a substituted benzyl.

35. A method according to claim 13, wherein said active ingredient is an A3 selective A3RAg that is selected from the group consisting of those of formula (IV) in which:

$X_1$ is $R^aR^bNC(=O)$, wherein $R^a$ and $R^b$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, and $C_3$–$C_{10}$ cycloalkyl, $R_2$ is selected from the group consisting of hydrogen, halo, $C_1$–$C_{10}$ alkyoxy, amino, $C_2$–$C_{10}$ alkenyl, and $C_2$–$C_{10}$ alkynyl, and $R_4$ is selected from the group consisting of R- and S-1-phenylethyl, an unsubstituted benzyl group, and a benzyl group substituted in one or more positions with a substituent selected from the group consisting of $C_1$–$C_{10}$ alkyl, amino, halo, $C_1$–$C_{10}$ haloalkyl, nitro, hydroxy, acetamido, $C_1$–$C_{10}$ alkoxy, and sulfo.

36. A method according to claim 35, wherein said active ingredient is an A3 selective A3RAg that is selected from the group consisting of those of formula (IV) in which:

$R^a$ and $R^b$ are the same or different and are selected from the group consisting of hydrogen and $C_1$–$C_{10}$ alkyl, and $R_2$ is hydrogen or halo;

$R^a$ is hydrogen, $R_2$ is hydrogen and $R_5$ is unsubstituted benzyl;

$R^b$ is $C_1$–$C_{10}$ alkyl or $C_3$–$C_{10}$ cycloalkyl and $R_5$ in R- or S-1-phenylethyl or a benzyl substituted in one or more positions with a substituent selected from the group consisting of halo, amino, acetamido, $C_1$–$C_{10}$ haloalkyl and sulfo, wherein the sulfo derivative is a salt;

$R_2$ is a $C_2$–$C_{10}$ alkyne of the formula $R^d$—C≡C— where $R^d$ is a $C_1$–$C_8$ alkyl; or $R_2$ is a halo, $C_1$–$C_{10}$ alkylamino, or $C_1$–$C_{10}$ alkylthio, $R^a$ is hydrogen, $R^b$ is $C_1$–$C_{10}$ alkyl and $R_5$ is a substituted benzyl.

37. A method for inhibiting abnormal cell proliferation in a subject in need thereof, comprising administering to the subject an adenosine A3 receptor agonist (A3RAg) in an amount of less than 100 µg/Kg body weight.

38. A method according to claim 37 wherein the amount of the A3RAg is less than 50 µg/kg body weight.

* * * * *